United States Patent [19]

Hughett et al.

[11] Patent Number: 5,681,330
[45] Date of Patent: Oct. 28, 1997

[54] STERILE OCCLUSION FASTENERS AND INSTRUMENT AND METHOD FOR THEIR PLACEMENT

[75] Inventors: J. David Hughett, Hamilton; David Stefanchik, Mason, both of Ohio; Michael A. Murray, Bellevue, Ky.; C. Kerwin Braddock, Cincinnati, Ohio

[73] Assignee: Ethicon Endo-Surgery, Inc., Cincinnati, Ohio

[21] Appl. No.: 726,141

[22] Filed: Oct. 4, 1996

Related U.S. Application Data

[63] Continuation of Ser. No. 403,983, Mar. 15, 1995, abandoned, which is a continuation-in-part of Ser. No. 204,847, Mar. 2, 1994, abandoned.

[51] Int. Cl.⁶ .................................................. A61B 17/00
[52] U.S. Cl. .................. 606/143; 606/139; 606/151; 227/901
[58] Field of Search ............................ 606/143, 142, 606/139, 151; 227/175.1–182.1, 19, 901

[56] References Cited

U.S. PATENT DOCUMENTS

| | | |
|---|---|---|
| 648,841 | 5/1900 | Brosnan . |
| 1,458,797 | 6/1923 | Beale . |
| 2,874,384 | 2/1959 | Krone ................................... 1/49 |
| 3,023,463 | 3/1962 | Hord et al. ......................... 22/116 |
| 3,032,039 | 5/1962 | Beaty . |
| 3,518,993 | 7/1970 | Blake . |
| 3,827,277 | 8/1974 | Weston . |
| 4,017,337 | 4/1977 | Winter et al. .................. 148/11.5 A |
| 4,086,926 | 5/1978 | Green et al. ..................... 128/344 R |
| 4,325,377 | 4/1982 | Boebel ............................... 606/142 |
| 4,493,319 | 1/1985 | Polk et al. . |
| 4,624,254 | 11/1986 | McGarry et al. .................. 128/325 |
| 4,671,278 | 6/1987 | Chin . |
| 4,674,504 | 6/1987 | Klieman et al. .................. 606/143 |
| 4,791,707 | 12/1988 | Tucker ............................... 227/19 |
| 4,796,627 | 1/1989 | Tucker . |
| 5,026,379 | 6/1991 | Yoon .................................. 606/141 |
| 5,192,288 | 3/1993 | Thompson et al. ................. 606/143 |
| 5,207,692 | 5/1993 | Kraus et al. ....................... 606/143 |
| 5,217,473 | 6/1993 | Yoon .................................. 606/157 |
| 5,282,811 | 2/1994 | Booker et al. ..................... 606/143 |
| 5,342,373 | 8/1994 | Stefanchik et al. ................ 606/142 |
| 5,364,002 | 11/1994 | Green et al. ....................... 606/143 |
| 5,366,134 | 11/1994 | Green et al. ....................... 227/182 |
| 5,395,381 | 3/1995 | Green et al. ....................... 606/143 |
| 5,474,567 | 12/1995 | Stefanchik et al. ................ 606/143 |

FOREIGN PATENT DOCUMENTS

| | | |
|---|---|---|
| 0 121 474 | 10/1984 | European Pat. Off. ......... A61B 17/12 |
| 0 552 050 A2 | 7/1993 | European Pat. Off. ......... A61B 17/00 |
| 2 141 219 | 3/1972 | Germany . |
| 27 30 691 | 1/1978 | Germany ...................... A61B 17/12 |
| 30 44 186 A1 | 8/1981 | Germany ...................... A61B 17/12 |
| 40 15 562 | 11/1991 | Germany ...................... A61B 17/10 |
| WO 82/01125 | 4/1982 | WIPO ........................... A61B 17/10 |
| WO 88/01487 | 3/1988 | WIPO ........................... A61B 17/10 |
| WO 93/20756 | 10/1993 | WIPO ........................... A61B 17/00 |
| WO/95/05778 | 3/1995 | WIPO ........................... A61B 17/12 |
| WO 96/10365 | 11/1996 | WIPO .......................... A61B 17/128 |

OTHER PUBLICATIONS

EPO Search Report.

*Primary Examiner*—Jeffrey A. Schmidt
*Attorney, Agent, or Firm*—Susan M. Schmitt

[57] ABSTRACT

A clip applier and method for ligating a tissue structure is provided. The applier has a two stage actuation. In the first stage, a tissue structure is positioned into the jaws of the clip applier. The jaws close and lock to a preset force to compress and temporarily occlude the tissue structure. If satisfactorily positioned, the second stage is initiated in which a clip is advanced through the shaft of the clip applier in a closed position. At the distal end of the clip applier, the clip is opened slightly to capture the pre-compressed tissue structure, and is placed over the structure. The clip is then dissociated from the business end of the instrument. Preferably the clip comprises two leg members disposed in close proximity to one another joined from opposing directions by a connecting element. The connecting element restricts separation of the leg members with opposing spring members so as to provide substantially uniform parallel deflection of the leg members from each other.

11 Claims, 14 Drawing Sheets

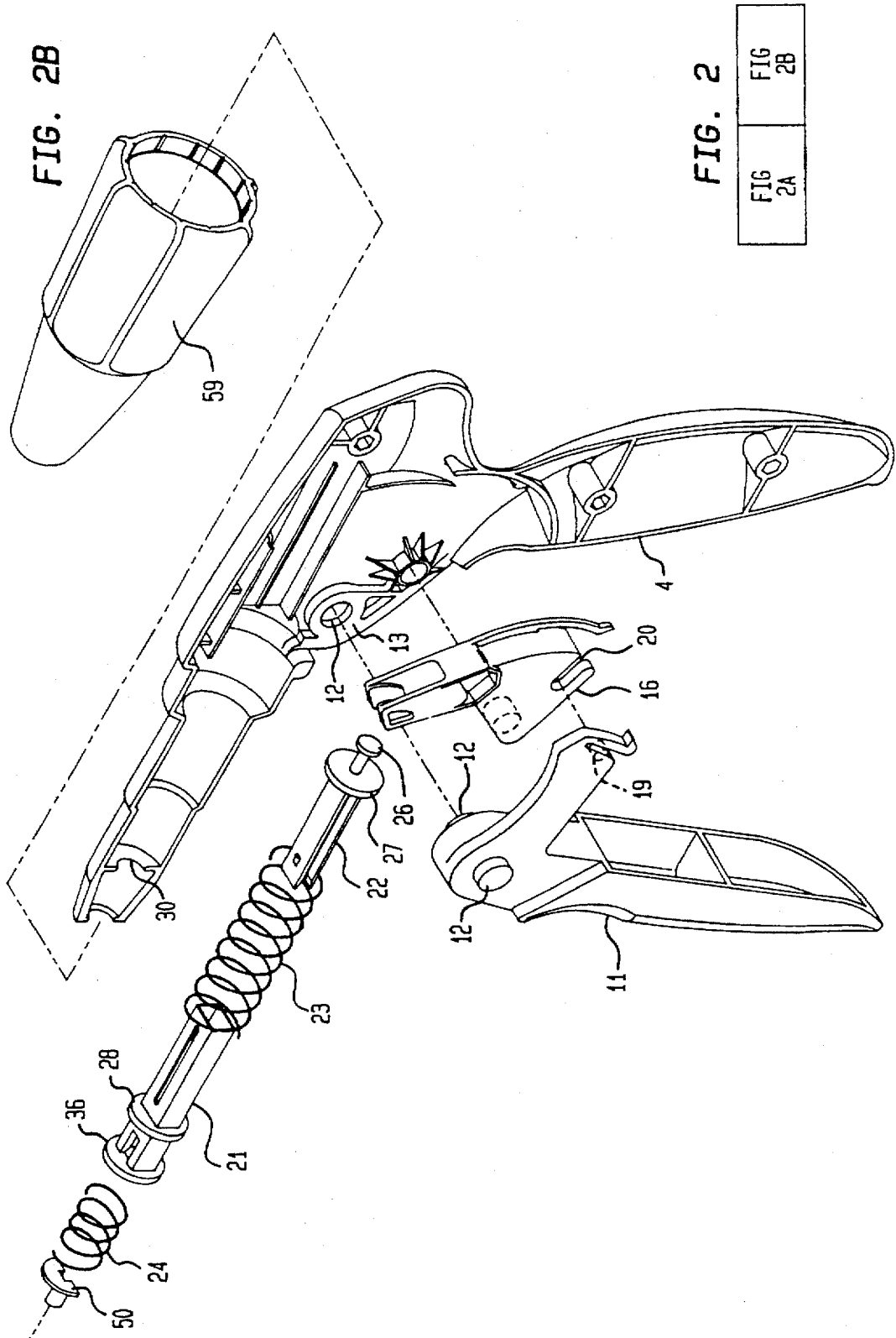

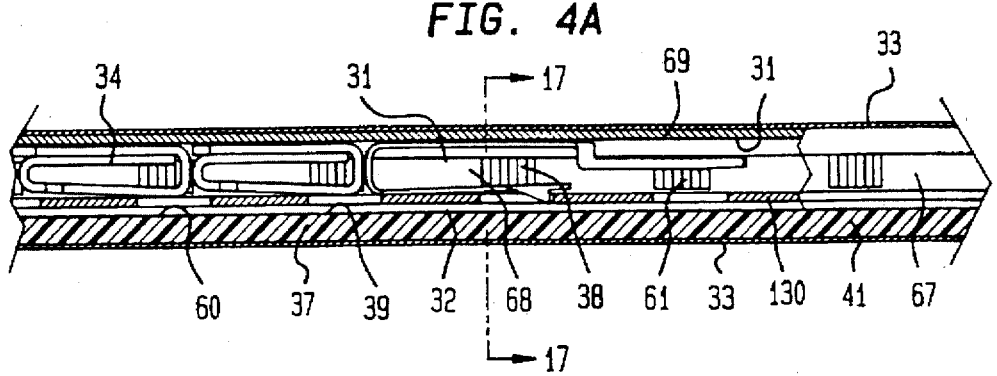
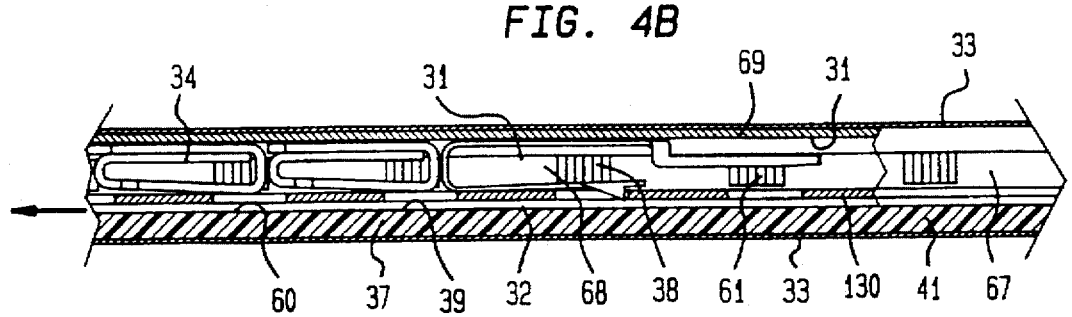
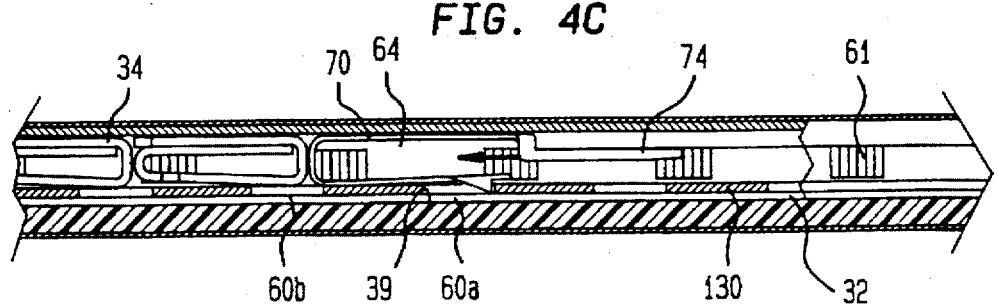
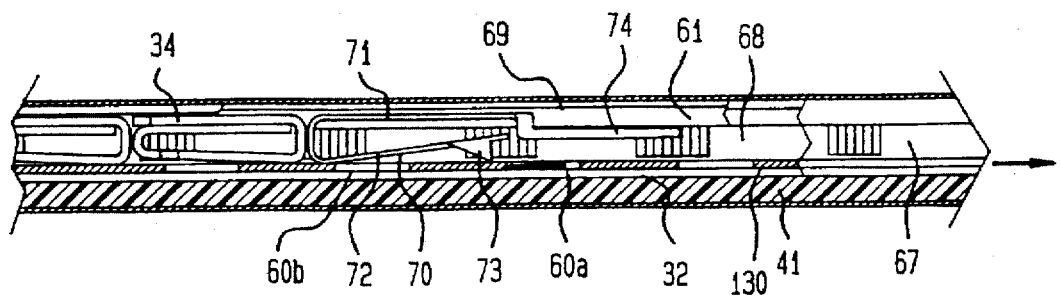

STERILE OCCLUSION FASTENERS AND INSTRUMENT AND METHOD FOR THEIR PLACEMENT

This is a continuation of application Ser. No. 08/403,983, now abandoned but filed Mar. 15, 1995 which is a continuation in part of application Ser. No. 08/204,847 filed on Mar. 2, 1994, now abandoned but incorporated herein by reference.

BACKGROUND OF THE INVENTION

The present invention relates to sterile surgical fasteners, used to occlude bodily tissue structures, and the methods and instruments for applying such fasteners. More particularly, this invention relates to sterile clips, and instruments and methods for placement of such clips, that are used to ligate tubular structures within the body, such as blood vessels, to impede the flow of bodily fluid therethrough.

In order to prevent excessive fluid loss or bleeding during a surgical procedure, a surgeon will typically have to ligate or close various fluid ducts and/or blood vessels before severing those vessels. There are many types of mechanisms or devices for shutting off the vessels such as ligating clips, hemostatic clips and the like. In some instances the surgeon will tie a ligature or suture about a vessel to close or shut the vessel. Ligating clips are well known in the art. Many of the clips are metal and comprise a pair of legs which are connected at one end. The Vessel to be ligated is placed between the legs and the legs forced together about the vessel to close the vessel. Clips have also been developed from plastic materials. However, since plastics do not have the same strength and malleability characteristics as metals, the plastic clips typically include some type of locking mechanism so that when the legs are urged together about the vessel they are locked in a closed position.

Ligating clips should ensure closure of the vessel. That is, they should completely shut off blood flow or other fluid flow and not allow leakage. Also, the clips should remain closed, should not open or break and should not slip or slide out of position or off the vessel. While it doesn't take much force to collapse and close a vessel, the clips that are now typically used require substantial force to close or change configuration so that once closed, the clip will remain in its closed position.

In minimally invasive surgery, in particular, endoscopic surgery, it has become desirable to provide smaller instruments capable of reaching surgical sites through smaller access ports. Smaller incisions cause less damage in accessing the surgical site and the access wounds from such incisions heal faster. In presently known clip appliers, the size of the instrument is dictated, in general, by the size of the clip as it is passed through the clip applying instrument to its business end, and the size of the jaws used to crush the clips closed. Clips are passed through the clip applying instrument in an open position so as to allow the clip to capture a tissue structure to be ligated before the jaws crush the clip closed over the structure.

In currently used surgical access tubes or cannulas and clip applying instruments for use in endoscopic or laparoscopic surgery, the ratio of the cannula inner diameter to the closed clip height as defined herein, is greater than 7.0. Thus, presently, a relatively large access tube is required for relatively small closed clip height.

It is therefore an object of the invention to provide a clip which is contained in a space-efficient, closed position until it reaches the structure to be ligated, thus enabling the use of smaller access ports.

In endoscopic surgery, the business end of the instrument is placed within the body through an appropriate cannula, body canal or small incision. The manipulation of that business end by the surgeon is accomplished outside the body. As a result, it becomes more difficult to control the business end of the instrument since it is further removed from the actual operation of the instrument. Any slight movement in the manipulation of the instrument outside the body is magnified at the business end of the instrument. Therefore, there is a greater chance in an endoscopic procedure that a slight movement of a clip applier as a clip is being closed will cause clip misplacement. This is particularly true considering that conventionally available clips require high force to effectively form over a tissue structure.

It is therefore another object of the present invention to substantially reduce the forces required to endoscopically apply a clip to ligate a structure such as a blood vessel. The less force required to place a clip, the greater the chance of accurate clip placement and therefore of positive vessel closure throughout the surgical procedure. Further, the force used to crush the clip also crushes the tissue, making the clip hard to remove, if so desired. Also, the less force required to place a clip on a vessel, the less likely the vessel will be cut or lacerated.

It is a further object of the present invention to provide a clip and clip applier which allow a user to close off a vessel and determine whether the positioning is appropriate before applying the ligating clip.

Clips now typically used are applied with a clip applier which crushes the clip to a preset dimension. Although a range of clip sizes exist to provide for ligation of a variety of tissue structure sizes, frequently, the preset dimension is too large for a smaller structure or too small for a larger structure. If the structure is too small or too large, or conversely stated, if the clip gap of the closed gap is too large or too small, the clip has a greater chance of being misplaced, of providing inadequate ligation force or of slipping off the vessel.

Furthermore, the presently used clips typically comprise two legs attached at one end. Therefore, the closure force varies along the length of the clip, the greater force being closer to where the legs are attached. Thus with such a clip configuration, the chances are greater that the clip will slip from the closure site, particularly if the tissue is slightly misplaced towards the clip opening.

It is therefore an object of the invention to provide a clip and applier which reduce the chances of the clip slipping from the ligated vessel site or of providing insufficient ligation. It is an object of the invention to provide a clip and a method of applying the clip to a wider range of vessel sizes. It is also an object of the invention to provide a clip which provides substantially uniform ligating force along the length of the clip.

Though the novel clip, instrument and methods of the present invention are most appropriate for use in endoscopic procedures and will be so described in the following, it should be pointed out that the clip and/or the instrument could also be used quite capably in traditional open type surgical procedures.

SUMMARY OF THE PRESENT INVENTION

In accordance with the present invention, a new sterile clip, clip applier and method for ligating a tissue structure is provided.

One embodiment of the invention provides compression members at the distal end of a clip applying instrument which compress and/or occlude a tissue structure just prior to applying a ligating clip.

One feature of a preferred embodiment provides a clip applier which ligates or compresses a tissue structure to a predetermined force as opposed to a specific gap size or range before advancing a ligating clip to the structure.

Another feature of a preferred embodiment provides an efficiently sized clip, which may be passed to the distal end of the clip applier in a closed position. When the clip reaches the distal end of the instrument, it may be slightly opened, sufficiently to capture tissue which has been compressed and/or occluded. Then, the clip is released from the business end of the device, and, because the material of which it is constructed retains its resiliency and yields very little, the clip tends to return to its original shape, thereby keeping the ligated structure occluded.

The clip and instrument of the present invention may be used in smaller diameter cannulas than prior art clips and clip applying instruments used to close the same size vessels. For example, a clip or a clip applying instrument typically requiring a 10 mm cannula inside diameter, may now only require a cannula having an inside diameter of approximately 5 mm. An object of the invention is to provide device in which a smaller size trocar may be used in conjunction with the clip applier for a desired clip use.

Ideally the ratio of the cannula size (cannula inner diameter) to closed clip height is as close to unity as possible. For medium-large sized clips, the maximum ratio of cannula size to closed clip height is preferably about 2.7. The maximum ratio of cannula size to closed clip height for the medium sized clip is preferably about 3.2. The maximum ratio of cannula size to closed clip height for the small sized clip is preferably about 5.6. The clip sizes defined herein are intended to generally reflect the clip sizes known in the art and currently used in disposable clip appliers for laparoscopic and endoscopic surgery.

A preferred embodiment of this aspect of the invention is in use with the clip of the present invention advanced through the instrument in its closed or semi-closed configuration. Using a closed configuration, no jaws are necessary to contact the clip in order to close the clip, the overall diameter of the instrument may be reduced when compared to prior art instruments used for the same function. This allows the instrument to be used in smaller size access channels, incisions and/or cannulas and reduces the size of the incision in the patient. For example, currently used endoscopic clip appliers are about 10 mm in outside shaft diameter. A 5 mm outside shaft diameter clip applier and clip of the present invention may be used to apply clips presently only capable of being used only with a 10 mm or larger size access tube and clip applier, for example, clips of a 8–9 mm closed length size.

Ideally, the ratio of the diameter of the clip applier shaft to the final clip configuration height is as near unity as possible, taking into consideration various design constraints. The final clip configuration height is defined herein to mean the height of the clip measured in a plane perpendicular to the ligating surfaces when the clip is closed over a tissue structure. The present invention more specifically provides a clip applier and a clip wherein the ratio of the outer diameter of the clip applier shaft to the final clip configuration height is less than 5.2, preferably less than about 3.0 and most preferably less than 2.6. These preferred ratios have been determined based on conventional clip sizes and conventional instrument and access tube sizes.

The clip applier of the present invention may be adapted to receive clips of various sizes. However, the clip of a preferred embodiment, itself, is adapted to receive a range of various vessel sizes. This clip tends to size itself as it is placed on the vessel. This feature provides a clip having a preloaded force which will not yield when the clip is deflected slightly, but sufficiently to capture a tissue structure.

The clip as such is formed of a resilient (as opposed to malleable) material and has tissue occluding leg members biased to spring back to a near zero gap size. The legs of the clips are biased together with a given force and the force increases at increasing deflection. The leg members include opposing ligating surfaces.

One embodiment of the invention provides a clip which is deflected from multiple clip elements, so as to divide the deflection force between multiple opposing springs, among other reasons, to reduce the likelihood of the clip yielding. For example, the clip may be deflected from two ends so as to divide the deflection force between two springs. The springs are arranged with respect to the ligating surfaces to permit deflection and closure of opposing ligating surfaces away from and towards each other, respectively. The springs are arranged so that opposite ligating surfaces provide sufficiently uniform force to close off a tissue structure placed therebetween. Preferably, the ligating surfaces of the clip are biased towards each other but from directionally opposite ends, so as to provide more uniform force between surfaces over the length of the clip.

In one embodiment, a one piece clip is provided with a plurality of opposing springs or spring force directions associated with opposing ligating surfaces.

In a preferred embodiment the clip comprises two leg members disposed in close proximity and substantially parallel to one another at least along the portion of their lengths where a tissue structure is to be captured and ligated. The leg members are connected to each other by a connecting element which restricts separation of the leg members. The connecting element and leg members provide an opening at the distal end of the leg members, for capturing a tissue structure between ligating surfaces associated with the leg members. The connecting element, with which the springs are associated, allows the distal ends of the leg members to be slightly pushed apart by forces applied to the clip. Once those forces are removed the leg members return toward their original position.

In one embodiment, two opposing parallel leg members are joined by a connecting element having at least two springs acting from different directions on directionally opposed leg members. Preferably, two diametrically opposing spring members provide substantially parallel uniform deflection of the leg members from each other. A first spring member permits a first parallel leg to deflect away from a second parallel leg at the distal end of the clip. The second spring member permits the second parallel leg to deflect from the first parallel leg member proximal of the distal end of the clip. Preferably one of the two spring members is on a distal end of the clip while the other spring member is located at or towards the proximal end. The parallel legs provide an opening on the distal end of the clip for receiving tissue to be ligated. The opening may be angled to gather or "funnel" tissue between leg members, or, when being applied, may be opened by the applying mechanism to funnel tissue.

In a preferred embodiment, each leg member has at least one free end associated with it, such that the free ends of each leg member are opposed, irrespective of where connected. Preferably, the leg members are cantilevered from both the distal and proximal ends of the clip, one leg member from one end and the other leg member from the other end, so that the free end of one leg member resides at a restricted end of the other leg member, and vice versa. The connecting element restricts and connects each leg member at the leg member's restricted end. In this embodiment, the leg members are oriented so that their distal and proximal ends directionally correspond to the distal and proximal ends of a clip applying instrument wherein the distal end of the instrument includes the business end of the device.

The present invention also includes an instrument and method for applying the sterile clip to a vessel to be ligated. The instrument includes a handle having an actuating trigger and an elongated shaft with jaw members at its distal end. The jaw members comprise a pair of occluding surfaces diverging from each other from their proximal end to their distal end. These surfaces are arranged to accept a vessel to be ligated. The surfaces may be placed on opposite sides of the vessel to be ligated and occlude the vessel.

In operation, jaws of the instrument are placed through an access channel or port such as a cannula. The jaws of the instrument are positioned about the tissue or structure to be ligated. The jaws of the instrument may be rotated using a knob accessible by the instrument user, to rotate up to 360 degrees in either direction, to assist in positioning the jaws about the tissue or structure to be ligated, and to provide operative site visibility and accessibility. The jaws are preferably biased apart by a spring having a predetermined force. The spring loaded jaw closing mechanism closes the jaws to a predetermined force. The jaws may be locked in their closed position before the clip is placed over the tissue structure.

Once the jaws are positioned, the trigger may be actuated to close the jaws over the tissue or structure and thereby temporarily occlude the tissue. At this point, the user may examine: whether the appropriate tissue is compressed; whether sufficient or excessive tissue is compressed; and whether or not there is sufficient compression, all accomplished before applying the clip to the tissue. If the user is not satisfied, the trigger may be released to open the jaws of the instrument disengaging it from the tissue or structure without having applied a clip. If the user is satisfied, the ratcheted trigger is squeezed further. The clip is passed to the end of the instrument which spreads the legs of the clip slightly so that the opening at the distal end of the clip can accept the tissue structure at or near where the diverging surfaces have compressed and occluded the tissue structure. The clip is advanced over the tissue and then is disassociated from the jaws of the instrument. Following release of the trigger, the jaws may be removed from the tissue while the clip remains on the ligated vessel.

One embodiment of the invention provides an applier having a single-trigger, two stage actuation stroke for; 1) grasping and positioning of the tissue into the instrument to find the appropriate clip position and compressing tissue; and 2) locking the device and advancing the clip onto the tissue.

In one embodiment, the second stage comprises advancing the distal clip and moving the clip stack with slightly delayed timing.

Another embodiment may include a plurality of triggers used to actuate the functions of the instrument described herein. For example, a first trigger is associated with a tissue compressing means and a second trigger is associated with a feed means. The first trigger is actuated causing the tissue compressing means to compress tissue at the distal end.

Then, the feed means feeds a fastener to the distal end of the instrument where the fastener is placed over the pre-compressed tissue and dissociated from the instrument.

An alternative embodiment provides an instrument which applies a clip to a pre-compressed tissue structure. The clip may be shaped like a conventional clip but in a semi-formed state so as to reduce the size of the clip as it is passed to the end effector of the instrument. A compression means of the end effector pre-compresses the tissue structure prior to closing the ligating clip over the tissue. The tissue may be released from the compression means of the end effector prior to applying the clip. The clip has an opening just large enough to fit over the pre-compressed tissue. After advancing the clip over the pre-compressed tissue, the end effector then crushes the clip closed, thereby ligating the tissue structure.

The invention will be more fully described in conjunction with the specific embodiments given in the following drawings and description.

BRIEF DESCRIPTION OF THE DRAWINGS

FIGS. 2A and 2B are an exploded perspective view of a preloaded clip applier of a preferred embodiment of the invention.

FIG. 4A is a side cross sectional view of a portion of the shaft of the present invention in a resting position.

FIG. 4B is side cross sectional view the portion of the shaft of FIG. 4A with a feed bar advancing the distal most clip in front of the feed bar.

FIG. 4C is side cross sectional view the portion of the shaft of FIG. 4A with a feed plate advancing a stack of clips.

FIG. 4D is a side cross sectional view of the portion of the shaft of FIG. 4C with the feed plate and feed bar returning to their original resting positions.

DETAILED DESCRIPTION OF THE INVENTION

Figure 11:
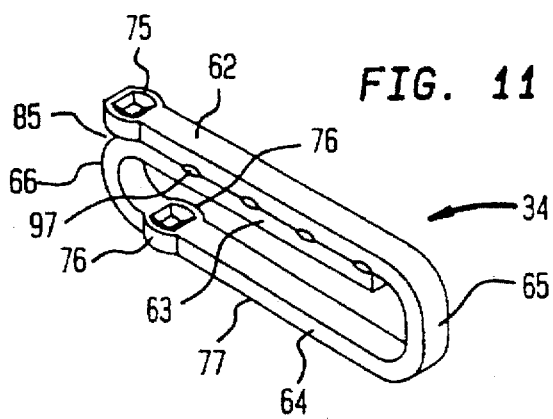
FIG. 11 is a perspective view of the clip of a preferred embodiment.

Referring now to FIG. 11 there is illustrated a clip 34 of the present invention. The clip 34 comprises a top leg member 62, a connector portion 64, and a second leg member 63. The connector portion 64 comprises an elongated portion 77 and two spring members 65,66. The first spring member 65 is located at the proximal end of the clip 34 and is coupled to the proximal end of the first leg member 62. The second spring member 66 is located at the distal end of the clip 34 and is coupled to the distal end of the second leg member 63. The first leg member 62 and the second leg member 63 are substantially parallel to each other along substantially their entire length. Each leg member 62,63 has a tissue engaging surface 78,79 respectively. Each tissue engaging surface interfaces with the tissue engaging surface of the other leg member. The tissue engaging surfaces 78,79 include scored surfaces 98 for holding tissue between the interfacing surfaces and preventing tissue from slipping out. The surfaces 78,79 may also have dimples 97 or the like to ensure closure and prevent movement of the clip 34 once it is placed on the tissue structure. The proximal ends of the leg members 62,63 form an opening 85 for capturing a tissue structure 99 (FIG. 5) such as a tubular vessel. The top leg member 62 includes two upper transverse tabs 75 located at the distal end of the top leg member 62. The connector portion 64 includes two lower transverse tabs 76 located towards the distal end of the connector portion 64. The clip has a height, h. The height is measured in a plane perpendicular to the ligating surfaces when the clip is passed through the shaft 5, prior to placement over a tissue structure.

The clips of the present invention are preferably made from various well-known materials or alloys of materials, for example, of titanium, tantalum, stainless steel, memory metals having super elastic characteristics or the various plastic materials that have some resiliency such as polyolefins, glycolide-lactide polymers and similar plastic materials. The yield strength of the material should sufficient to allow opening by the instrument of the clip, to place it over tissue and resiliently return to its original closed configuration. Preferably, the material used is a titanium alloy, such as for example, titanium 3Al–2.5V.

Figure 12:
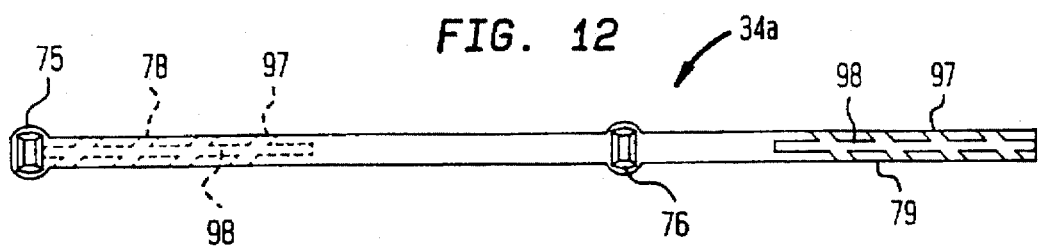
FIG. 12 is a top view of the clip of FIG. 11 prior to being preformed.
Figure 6:
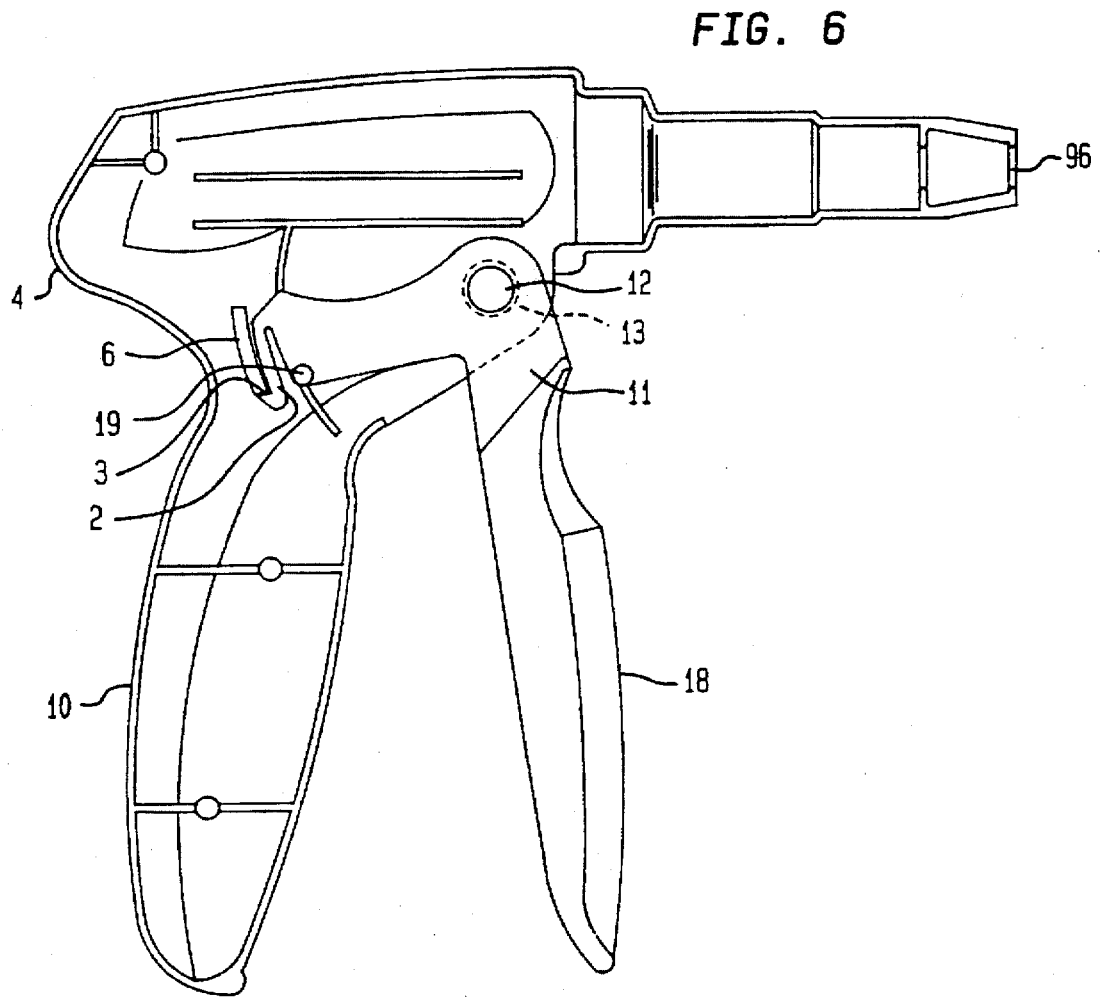
FIG. 6 is a side cross sectional view of the housing of the clip applier.
Figure 7:
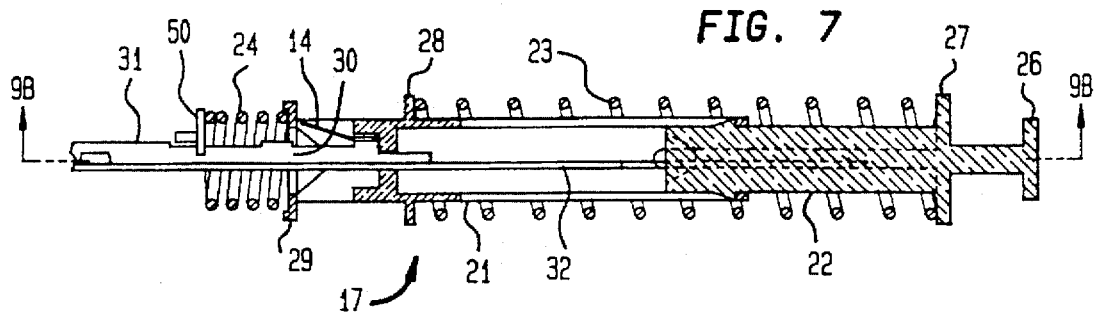
FIG. 7 is a side cross sectional view of the coupling mechanism of the clip applier.
Figure 8:
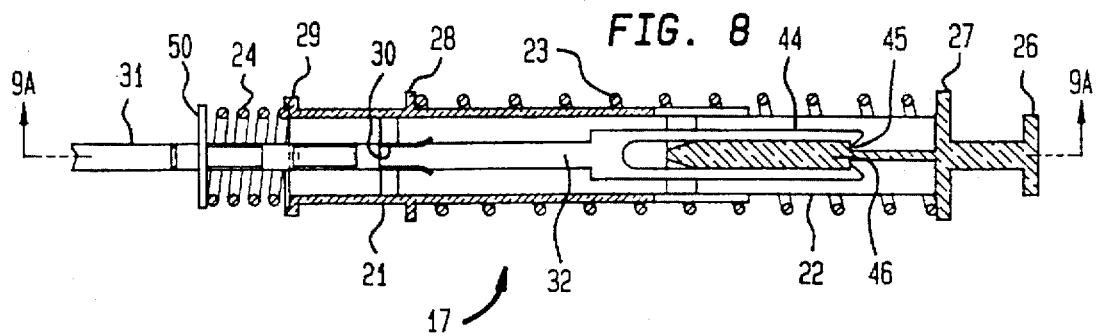
FIG. 8 is a top cross sectional view of the coupling mechanism of the clip applier.
Figure 9:
FIG. 9 is a perspective view of the lower jaw.
Figure 10:
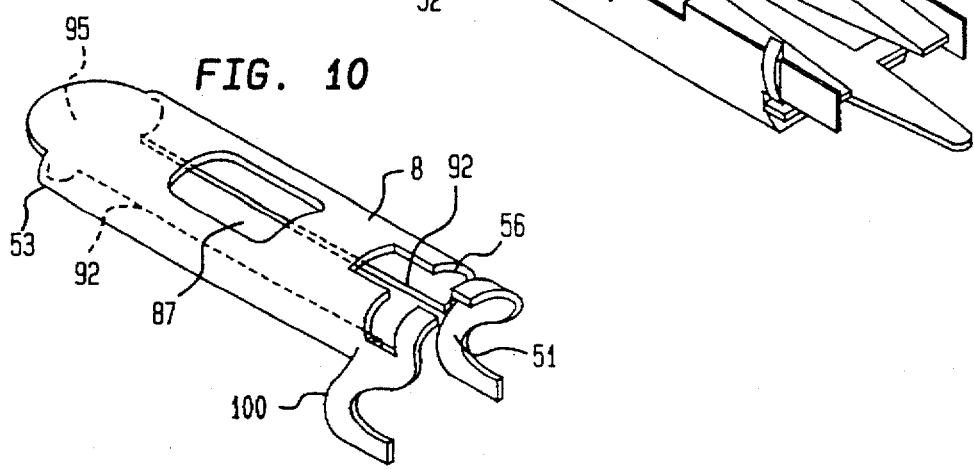
FIG. 10 is a perspective view of the top jaw.
Figure 13:
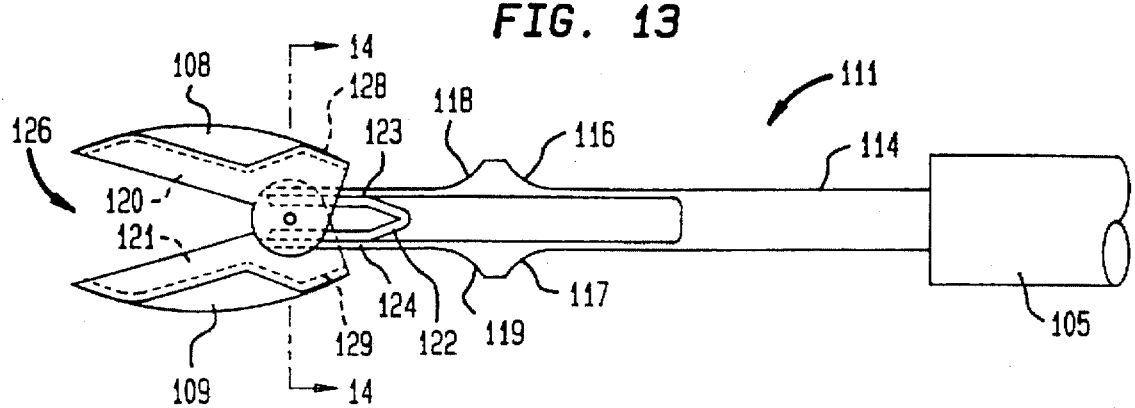
FIG. 13 is a partial breakaway side cross-sectional view of an end effector of an alternative embodiment of the present invention in its initial position.
Figure 14:
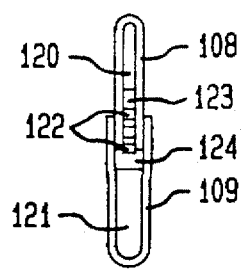
FIG. 14 is a cross section of the end effector of FIG. 13 along the lines 14—14.
Figure 15:
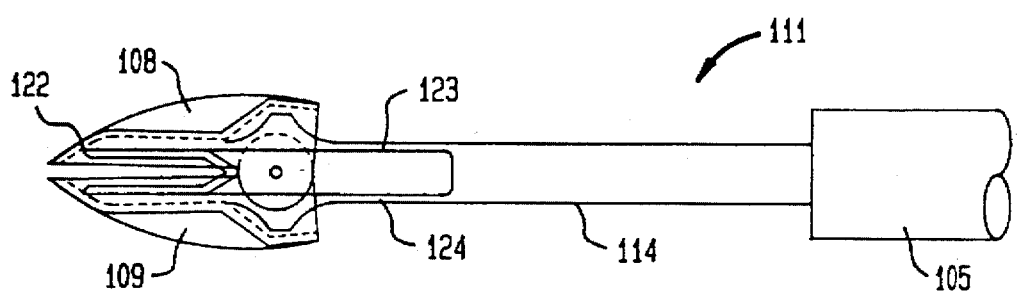
FIG. 15 is a partial breakaway side cross-sectional view of the end effector of FIG. 13 in a tissue compressing mode.
Figure 16:
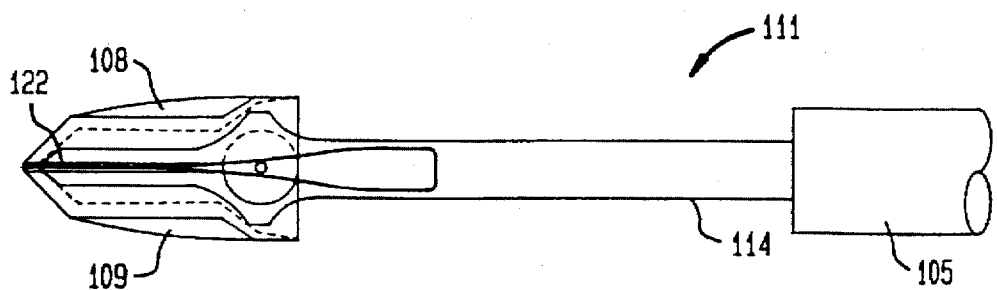
FIG. 16 is a partial breakaway side cross-sectional view of the end effector of FIG. 13 illustrating closure of a clip.
Figure 17:
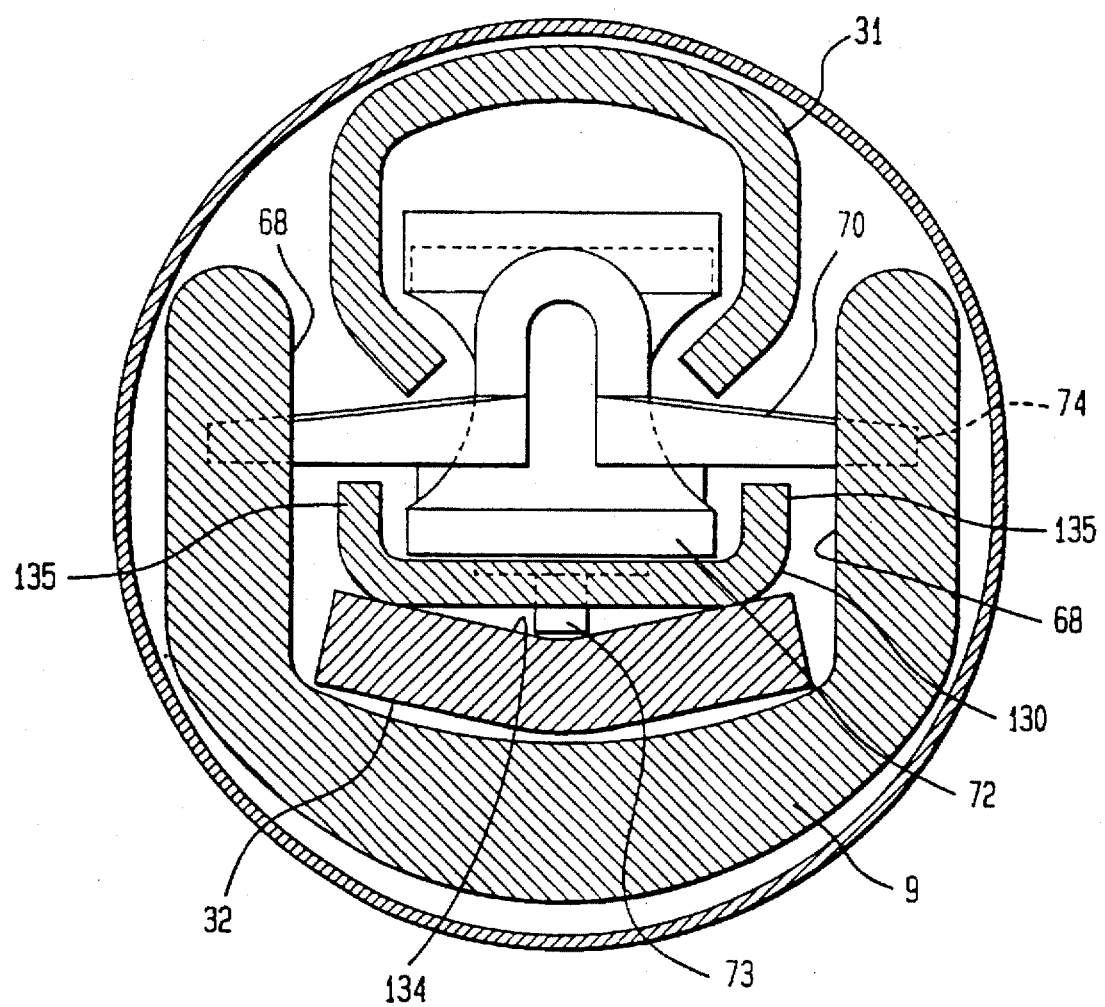
FIG. 17 is a transverse cross-section of the instrument of FIG. 4A along the lines 17—17.

FIG. 12 illustrates a titanium strip 34a prior to performing the clip 34 from the strip 34a. Transverse tabs 75,76 are formed in the titanium strip 34a by coining or other known manufacturing methods. The strip 34a is subsequently bent twice to form three substantially parallel portions, i.e., the leg members 62,63 and connector portion 64, and two bent portions, i.e., the springs 65,66. The bent portions act as springs biasing the respective ends of the attached leg member towards the opposite leg member, thus providing substantially uniform or substantially symmetrical biasing of the leg members towards each other.

Referring now to FIGS. 1–10, there is illustrated a clip applier 1 of the present invention. A housing 4 includes a stationary handle 10, a trigger 11 pivotally mounted to the housing 4, and a knob 59 rotatably attached to the distal end of the housing 4. The knob 59 and housing 4 are coupled to the proximal end of an elongated shaft 5. The shaft 5 includes a stationary elongated lower jaw portion 41 terminating in jaw 9, a grasper bar 31, a feed plate 130, a feed bar 32, a support tube 33, a stack 35 of clips 34, a feeder shoe 70 and, at its distal end 40, a pair of jaws 8, 9 for grasping and compressing a tissue structure 99 to be ligated.

The outer diameter, $D_S$, of the shaft 5 comprises the support tube 33 having a lumen through which extend the lower jaw portion 41, grasper bar 31, feed plate 130, and feed bar 32. The support tube 33 terminates just proximally of jaws 8,9 to permit pivotal action of jaws 8,9. The support tube 33 is constructed to resist excessive torquing to and/or deflection of the various parts of shaft 5.

The support tube 33 and the lower jaw portion 41 are rotatably attached to the housing 4 by way of rotating knob 59. The knob 59 is attached to the support tube 33 by a tab snap fit between the opening inner diameter of the knob 59 and the outerwardly protruding tabs 49 at the proximal end of the support tube 33. Inwardly protruding lugs 48 of the knob 59 are rotatably engaged with outwardly protruding tabs 49 of the support tube 33. The knob 59 permits 360 degree rotation of the shaft 5 with respect to the housing 4.

The trigger 11 includes a trigger arm 18 extending from the housing 4 so that the user may hold the handle 10 and actuate the trigger 11 by grasping the trigger arm 18 with the same hand. Posts 12 molded into trigger 11 fit into bosses 13 molded into housing 4, so as to permit pivotal movement of trigger 11 with respect to handle 10.

Housing 4 further includes a feed cam 16 pivotally attached to the housing 4 and slidably coupled to the trigger 11. The feed cam 16 is coupled on one end to a coupling mechanism 17. The coupling mechanism 17 couples the force applied to the trigger 11 to the tissue grasping/compressing and clip advancing/placing functions of the device. The trigger 11 includes a trigger post 19 which moves within a slot 20 in the feed cam 16. The trigger 11 is actuated by applying a force to the trigger arm 18 to rotate the trigger arm 18 towards the handle 10. This force causes: the trigger 11 to pivot about posts 12; and the post 19 to move within the slot 20 to pivotally rotate the feed cam 16 with respect to the housing 4. The rotation of the feed cam 16 multiplies the trigger force translating it into longitudinal movement of the coupling mechanism 17 as described in more detail below.

The coupling mechanism 17 is arranged longitudinally with respect to the longitudinal axis of the shaft 5. The coupling mechanism 17 is comprised of a grasper coupling 21, a feeder coupling 22, an in-line spring 23 and a return spring 24. The proximal end of the feeder coupling 22 includes a rearward extending post 26, and a radially extending circular surface 27. The feed cam 16 has two radially extending arms 25 which straddle a proximal or rearward extending post 26 of the feeder coupling 22, and are slidably mounted between radially extending circular surface 27 and rearward extending post 26. The radially extending arms 25 translate the rotational movement of the feed cam 16 to longitudinal movement of the coupling mechanism 17.

Longitudinal movement of the coupling mechanism 17 comprises two distinct steps. The first step comprises compression of the return spring 24 which has a lower spring preload and/or a lower spring constant than the in-line spring 23, and therefore compresses with less force. The first step corresponds to the tissue grasping and compression step of the trigger actuation. The second step comprises the compression of the in line spring 23, in general, for the most part, after the return spring 24 has compressed. The second step corresponds to the clip advancement and placement and the stack advancement steps of the trigger actuation.

The distal end of the feeder coupling 22 is slidably fitted and longitudinally moveable within the proximal end of the grasper coupling 21. The grasper coupling 21 includes a radially extending circular surface 28. The in-line spring 23 is situated over the feeder coupling 22 and grasper coupling 21, and between circular surface 27 and circular surface 28. The in-line spring 23 acts on circular surface 27 and circular surface 28 to longitudinally bias feeder coupling 22 and grasper coupling 21 away from each other. The grasper coupling 21 includes a second radially extending circular surface 29 on its distal end. The proximal end of the return spring 24 abuts against the distal end of the second circular surface 29. The lower jaw portion 41 includes a circular surface 36 on its proximal end enclosed within rotation knob 59 of housing 4. The distal end of the return spring 24 abuts against the circular surface 36. Thus, the return spring 24 biases the grasper coupling 21 in a proximal direction away from the proximal end of the shaft 5, i.e., away from the circular surface 36 of the lower jaw portion.

As an initial force is applied to the trigger arm 18, the feed cam 16 advances the coupling mechanism 17, the return spring 24 compresses, and the grasper coupling 21 longitudinally advances. Upon application of an appropriate additional amount of force, the feeder coupling 22 will slide towards the grasper coupling 21 as the in line spring 23 compresses.

Tissue is grasped and compressed by the top jaw 8 closing towards the jaw 9 of the stationary lower jaw portion 41. An elongated portion 37 of the lower jaw member 41 extends through an aperture 30 in the housing 4 and an aperture 96 in the knob 59, and along the longitudinal axis of the shaft 5. The elongated portion 37 is formed in a u-shape by side walls 38 and floor 39. The elongated portion 37 ends in a lower jaw 9.

The grasper bar 31 is attached at its proximal end to the grasper coupling 21 and extends longitudinally through an opening 47 circular surface 36 and the elongated portion 37 of the lower jaw portion 41. The grasper bar 31 includes a ceiling 69 and two side walls 68 which curve towards each other to form a C-shape. The two side walls 68 fit inside and adjacent side walls 38 of lower jaw portion 41. The lower jaw portion side walls 38 include notched surfaces 61. Forward longitudinal motion of the grasper coupling 21 is transferred to the grasper bar 31.

The top jaw 8 is located at the distal end of the grasper bar 31. Downwardly extending posts 55 on the distal end of the grasper bar 31 are inserted into corresponding slots 56 of top jaw 8 to movably attach the grasper bar 31 to the top jaw 8. The top jaw 8 includes a pair of hooks 51 on each side of the proximal end of the jaw 8. The hooks 51 pivotally engage the lower jaw 9 at indentations 52 in lower jaw 9. The top jaw 8 and lower jaw 9 include interfacing tissue contacting surfaces 53,54, respectively. Jaw 8 includes a window 87 through which compressed tissue may be viewed during the tissue compressing stage, and where a clip may be viewed during the clip advancing stage.

Advancement of the grasper bar 31 pivots the top jaw 8 closed towards the lower jaw 9 so that the interfacing surfaces 53, 54 move together to compress any tissue structure engaged between jaws 8,9. In this embodiment the lower jaw 9 is stationary while the upper jaw 8 is movable with respect to the lower jaw 9. Surface 54 of jaw 9 includes a series of teeth or interruptions 57 in the surface that reduce the distal movement of tissue engaged or compressed by the jaws 8, 9 relative to the distal advancement of the clip 34 on the compressed tissue. The interruptions 57 assist in properly positioning the tissue for accurate placement of the clip 34 on tissue. A pair of proximal tissue stops 100 incorporated into fronts of hooks 51, prevent tissue from going into the device proximally of jaw 8. The interruptions 57 and tissue stops 100 properly place the tissue in the amount to be ligated, where the clip disengages from the device. This is particularly important as the clip 34 in this embodiment does not extend as long as the jaws 8,9.

Release of the trigger 11 releases the return spring 24, which causes the grasper bar 31 to retract and the top jaw 8 to open. The grasper bar 31 includes a downwardly extending tab 137 which slideably fits into notch 138 proximally located in feed plate 130 and notch 139 proximally located in feed bar 32. The tab 137 in the grasper bar 31 serves to provide positive and aligned retraction of the feed plate 130 and feed bar 32 with the grasper bar 31.

After the jaws 8, 9 close over a tissue structure 99 to be ligated, the trigger arm 18 is squeezed further initiate the second step, i.e., clip advancement and placement. As the trigger is squeezed, a step force arm 2 on the trigger 11 contacts a corresponding step force rib 6 on the housing 4. When the return spring 24 is compressed and the jaws 8,9 closed to the force of the return spring 24, a protrusion 3 on the step force arm 2 contacts the corresponding step force rib 6 which imparts an increase in the tactile force felt on the trigger arm 18 by the user. This increase in force denotes the separation between the jaw closing mode and the clip advancement mode in the two-stage, single stroke actuation. Similarly, the feed cam 16 has an anti back-up arm 14 with a protrusion 15 at its distal end. Anti back-up arm 14 contacts a corresponding backup rib 7 on the housing 4 to prohibit the reversal of the feed cam rotational motion. This occurs at the transition between the jaw closing mode and the clip advancement mode of the trigger stroke. The backup rib 7 measures a complete stroke of the trigger before it permits the anti back-up arm 14 to disengage therefrom, thus ensuring the clip 34 is properly advanced all the way onto the tissue, as described in more detail below.

Two engagement arms 44 with inwardly protruding tabs 45, extend from the proximal end of the feed bar 32. The engagement arms 44 extend through an opening in the distal end of the grasper coupling 21 into the feeder coupling 22. Feeder coupling 22 has a center rib section 46 which is straddled by the engagement arms 44 of the feed bar 32 and is engageably coupled by tabs 45. The feed bar 32 is advanced by the forward motion of the feeder coupling 22.

In the second mode, i.e., the clip advancement and placement mode, trigger arm 18 advances the feeder coupler 22 which advances the feed bar 32 which in turn, after a delay, advances feed plate 130. The feed plate 130 and feed bar 32 extend through the opening 47 in circular surface 36 and longitudinally between the elongated portion 37 of the lower jaw portion 41 and the grasper bar 31. The feed plate 130 is slideably coupled to the feed bar 32 with upwardly extending side walls 135 and a tab 131 extending downward from the feed plate 130 into a slot 132 in the feed bar 32. The feed bar 32 is arranged to permit the tab 131 to slide within the slot 132 until the feed bar 32 advances distally so that the proximal end 132a of the slot 132 engages the feed plate tab 131 causing the feed plate 130 to advance. The feed bar 32 ends in a slightly bent heel portion 43.

A stack 35 of clips 34 is preloaded into the clip applier in an end to end configuration along the longitudinal axis of the shaft 5.

During the second trigger step, the heel portion 43 advances the distal most clip into the jaws 8,9 and towards an engaged compressed tissue structure 99. The feed plate 130 advances the subsequent stack 35 of clips in a delayed manner after the feed bar 32 initially advances the distal most clip 34. The heel portion 43 continues to advance the distal most clip into the jaws 8,9 and over an engaged compressed tissue structure 99 as the feed plate 130 advances the stack 35.

The feed plate 130 sits on top of the feed bar 32 which sits on top of the floor 39 of the lower jaw portion 41. The stack 35 of clips 34 sits on top of the feed plate 130 between the feed plate 130 and the ceiling 69 of the grasper bar 31. The stack 35 is surrounded by the side walls 38 of the grasper bar 31 which form the C-shape of the bar 31. In the open state, the distal most clip 34 in the stack 35 is positioned distally beyond the distal end of the feed plate 130 and the heel 43 at the distal end of the feed bar 32 and just proximal of the lower jaw 9. The stack 35 of clips 34 with a feeder shoe 70 positioned proximal of the last clip in the stack 35, is advanced distally through the shaft 5 by the feed plate 130 which is advanced by the slot 132 of the feed bar 32 slideably engaging the tab 131 of the feed plate 130.

The feeder shoe 70 has a main body 71 and a cantilevered lower arm 72 biased away from the main body. A tab 73 extends downward from the lower arm 72 and engages in one of a longitudinal series of slots 60 in the feed plate 130, i.e., so that the feed shoe 70 is positioned just proximal of the last clip in the stack 35. The feed bar 32 includes a v-shaped indentation 134 which receives the tab 73 of the feeder shoe 70 when the tab 73 extends through a slot 60 in the feed plate 130. The feed shoe 70 further comprises transversely biased arms 74 extending from the sides of the feed shoe 70.

The body 71 of the feeder shoe 70 is contained and held in place by C-shape grasper bar 31. The cantilevered lower arm 72 is contained by side walls 135 of feeder plate 130. The arms 74 extend through an opening between the grasper bar 31 and feed plate 130 to side wall 38 of lower jaw 9.

During the resting stage and when the grasper bar 31 is advanced, the arms 74 are in contact with the notched surfaces 61 of the lower jaw sides walls 38. The arms 74 are biased outward to impede proximal movement of the feed shoe 70. The arms 74 permit distal movement of the feed shoe 70. The feed bar 32 is advanced, and the arms 74 of the feed shoe 70 pass over the walls 68 of the grasper bar 31. The arms 74 then engage the next set of notched surfaces 61 located distally a distance of about one clip length. The C-shaped walls 68 of the grasper bar 31 serve to prevent undesirable transverse movement of the feeder shoe 70 and maintains the sequential alignment of the clips in the stack 35 by guiding the clips as they are advanced.

When the feed bar 32 is advanced, the feed bar 32 moves distally to advance the distal most clip while the feed plate 130 and the stack 35 remain stationary. When the distal end 132a of the slot 132 contacts the tab 131, the feed plate 130 advances. The slot 132 and tab 131 provide a sequential separation of the two actions of feeding the distal most clip 34 in front of the feed bar 32 and advancing the stack 35. This feature reduces the possibility of clip jamming, among other things, from the effects of partially opening and closing of the trigger 11 during placement of the jaws 8, 9 over tissue.

When the feed plate 130 is advanced, the feed shoe 70 is advanced because the tab 73 is engaged in one of the feed plate slots 60. The upwardly extending walls 135 of the feed plate help guide the lower tabs 76 of the clip and the feeder shoe 70. The distal end of the feed shoe 70 advances the stack 35 of clips towards the distal end of the instrument. Each time the trigger 11 fully advances the feed plate 130 and feed bar 32, the feed shoe 70 advances by one clip length. The grasper bar 31 has a cantilevered lifter spring 86 located towards its distal end. The cantilevered lifter spring 86 extends down from the ceiling 69 of the grasper bar 31.

During the initial advancement of the grasper bar 31, the distal most clip is moved from the longitudinal plane of the stack 35 into the longitudinal plane of the feed bar 32. During the second step of the trigger stroke, distal end of the feed bar 32 advances the distal clip 34 into the jaws 8,9 which have closed over, compressed and temporarily occluded a tissue structure 99. After the first clip is placed, the feed plate 130 is advanced by continued distal movement of the feed bar 32 advancing the stack 35. The next distal most clip is moved downward from the feed plate 130 and in front of the feed bar 32 by the cantilevered spring 86, as the feed bar 32 and then feed plate 130 are retracted at the end of the trigger return. The cantilevered spring 86 prevents the distal most clip from retracting with the feed bar 32 and feed plate 130. Thus, the distal most clip in the stack 35 is transferred by the cantilevered lifter spring 86 after the second stage of the trigger stroke is completed and the trigger is returned to its original position.

A longitudinal channel 93 is formed in the lower jaw 9 through which a downwardly extending depression 88 of the feed bar 32 rides to ensure the proper placement of the distal end of the feed bar 32 with respect to the distal clip throughout clip advancement and placement. When the distal clip is lowered into the plane of the feed bar 32, the lower transverse tabs 76 ride on shelves 90 formed in the side walls 38 of the lower jaw 9. The shelves 90 interface with the inner surface of the lower transverse tabs 76. The upper transverse tabs 75 ride along ramps 91 which engage the inner surfaces of the upper tabs 75 and angle the upper tabs 75 towards the top jaw 8, causing the inner tissue engaging surfaces 78, 79 of the biased leg members 62, 63 to separate from each other to provide the opening 85. At the end of the ramps 91 the upper transverse tabs make a transition from the lower jaw 9 to rails 92 in the top jaw 8. The rails 92 engage the inner surface of the upper transverse tabs 75. Thus, the first tissue engaging surface 78 of the first leg member 62 is advanced into the top jaw 8 above the compressed tissue structure 99. The second tissue engaging surface 79 of the second leg member 63 is advanced into the lower jaw 9 below the compressed tissue structure 99.

Throughout the advancement of the clip, the body of the clip is contained within longitudinal channels 93 and 94 in the top jaw 8 and lower jaw 9, respectively. Upper transverse tabs 75 advance to openings 95 towards the distal end of the top jaw 8. The width of the opening 95 is greater that the inner width of the rails 92 and closely corresponds to the outside width of the upper transverse tabs 75. The tabs 75 disengage from the top jaw 8 as they are advanced through the opening 95, allowing the upper leg member 62 to resiliently move toward the lower leg member 63 and contact tissue structure 99 with the tissue engaging surface 78.

Likewise, at approximately the same time, lower transverse tabs 76 reach opening 96 towards the distal end of the lower jaw 9. The width of the opening 96 is greater that the inner width of the shelves 90, and closely corresponds to the outside width of the lower transverse tabs 76. This allows the tabs 76 to disengage from the lower jaw 9 through the opening 96, allowing the lower leg member 63 to resiliently move toward the upper leg member 62 and contact tissue with the tissue engaging surface 79. The position of the tabs 75,76 corresponds to the timing of leg member disengagement from the jaws 8,9 of the instrument, to correctly place the clip on the tissue. Although an upper and lower set of transverse tabs are shown, a number of combinations, including a single tab alone, are possible for disengaging a clip from the instrument.

In addition to the release of the upper and lower transverse tabs 75, 76 through openings 95, 96 respectively, the channel 94 in the lower jaw 9 curves upward at its distal end to urge the clip 34 upward as it is disengaged from the lower jaw 9. Also, a longitudinally positioned kickoff spring 101 placed on the floor 39 of the jaw 9 assists the release of the clip 34 from the instrument. The kickoff spring 101 is compressed downward as the clip 34 is advanced distally into jaws 8,9. As top jaw 8 opens, the force holding the clip against the kickoff spring 101 is released and the spring 101 urges the clip out of the jaws 8,9.

The kickoff spring 101 extends from distal end of floor 39 of lower jaw portion 41 through channel 94 of lower jaw 9 as follows. The kickoff spring 101 is located along the longitudinal axis of the front lower jaw 9. The kickoff spring 101 includes proximally located, transversely extending attachment tabs 101a which fix the spring 101 to slots 9a in lower jaw 9 and prevent longitudinal, distal and proximal movement of the spring 101. In a resting position, the kickoff spring 101 is resiliently biased upward and has an upper portion 101b which may be depressed towards the lower jaw 9 by a clip passing through the jaws 8, 9. As the spring 101 is depressed, the distal end of the spring 101 slides forward within the jaw 9. The spring has a downward angled distal surface 101c which flattens out as the clip passes over the spring 101. When the lower transverse tabs 76 of the clip 34 are released from the shelves 90, the kickoff spring 101 acts on the bottom of the clip to lift the clip away from the lower jaw 9. The distal surface 101c rises as the clip is released and prevents the clip from retracting proximally back into the jaw 9.

The stack 35 of clips 34 is moved sequentially until all clips have been dispensed. The shaft 5 includes a clip indicator 80 which allows the user to identify when there is approximately one unused clip remaining in the instrument 1. The clip indicator 80 comprises a longitudinally positioned hole 81 in the support tube 33 located towards the distal end of the support tube 33 and a corresponding hole 83 in the grasper bar 31. The feeder shoe 70 has a colored marker 89 which shows through the holes 81, 83 when the feeder shoe 70 passes underneath the holes 81, 83 as it is advanced distally. When the feeder shoe 70 passes the hole 81 and corresponding hole 83, one clip remains.

A track plug 50 is positioned within the opening 47 of the lower jaw 41 and within the proximal end of the grasper bar 31, to reduce the outward flow of body cavity gases through the opening 47. The plug 50 is held in place and motionless with respect to the longitudinal motion of the grasper bar 31 and feed bar 32 by return spring 24.

Although the instrument is shown to have one moveable and one stationary jaw, the instrument may have both jaws moving to close over tissue to be occluded.

Figure 3A:
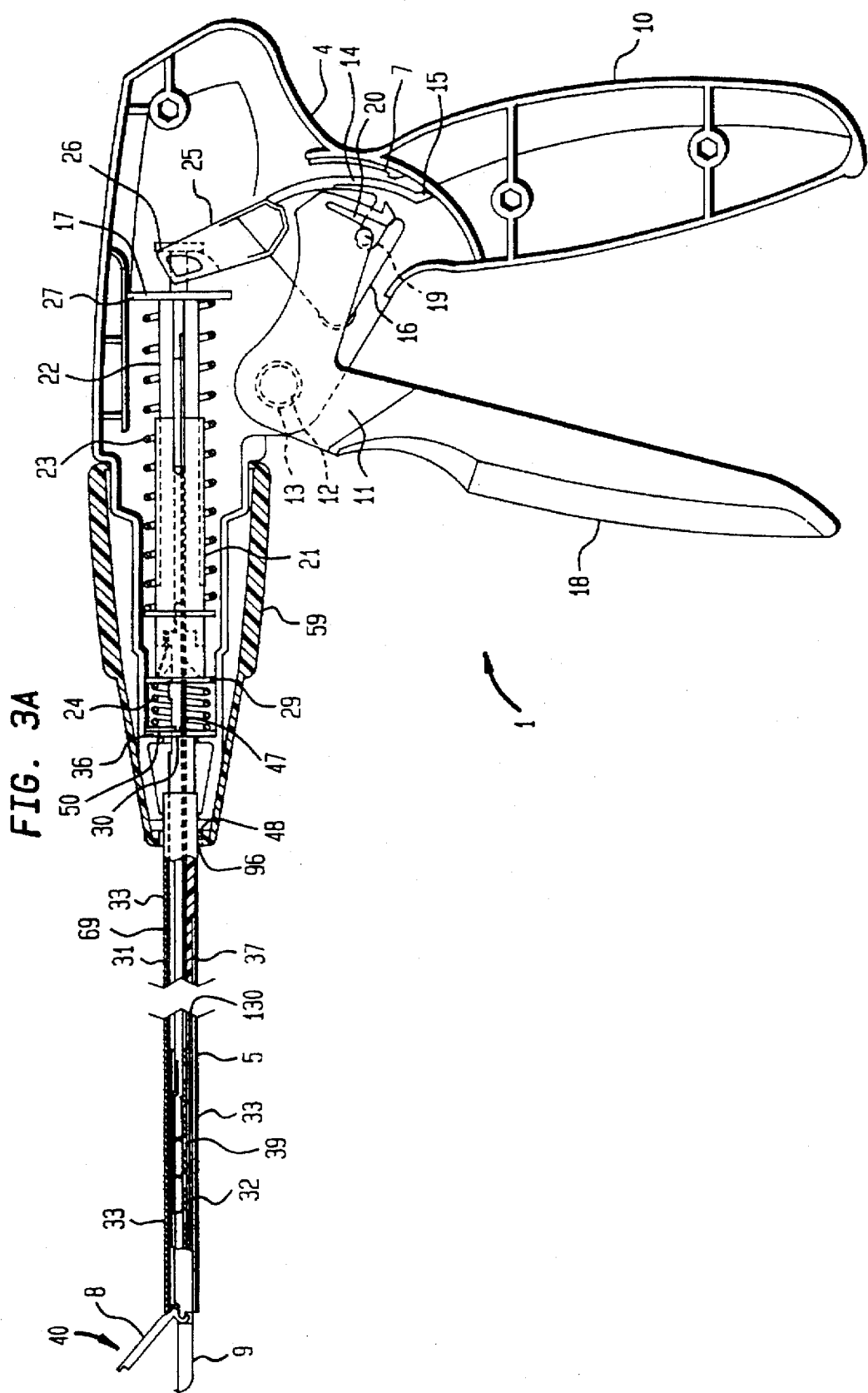
FIG. 3A is an enlarged cross sectional side view of the clip applier of FIGS. 2A and 2B in a resting position.

FIG. 3A illustrates a preferred embodiment of the clip applier 1 prior to actuation. At this stage, as further illustrated in FIG. 5A, the jaws 8,9 are open and may be placed about a tissue structure 99. FIG. 4A illustrates an enlarged cross section of the shaft 5 corresponding to the initial position of the device as illustrated in FIG. 3A. The transverse arms 74 of the feeder shoe 70 are engaged against the notched surfaces 61 of the lower jaw walls 68. The tab 73 extends downward from the lower arm 72 and engages in one of a longitudinal series of slots 60 in the feed plate 130 and extends into the v-shaped notch or indentation 134 of the feed bar 32.

Figure 3B:
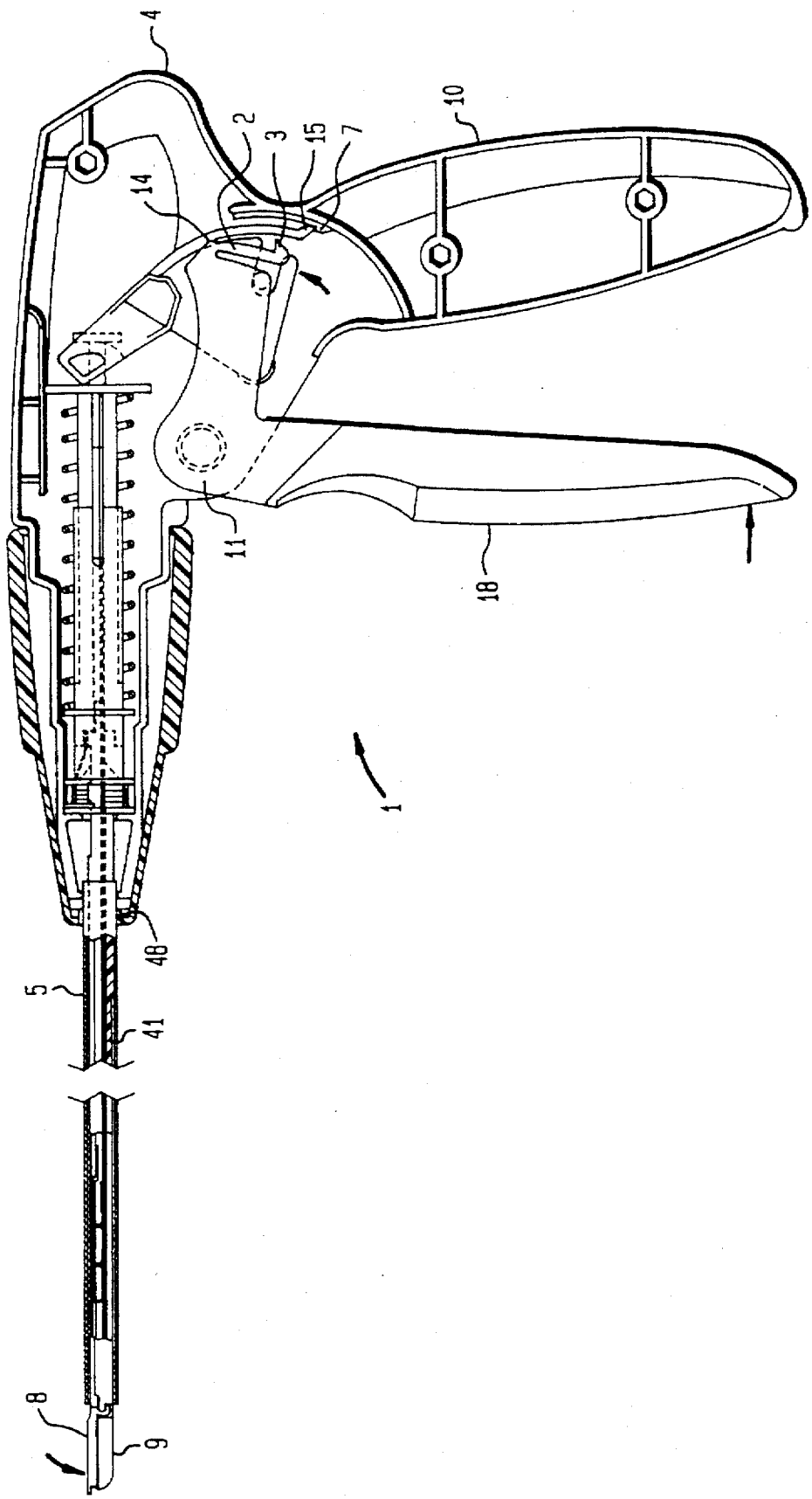
FIG. 3B is an enlarged cross sectional view of the clip applier of FIGS. 2A and 2B in a tissue grasping position at the end of a tissue grasping and compressing stage, and at the beginning of the clip advancement and placement stage of trigger actuation.

FIG. 3B illustrates the clip applier of FIG. 3A as it completes the tissue grasping stage of the trigger actuation. The protrusion 15 on the anti back-up arm 14 of the feed cam 16 has just engaged with the rib 7 of the housing. Thus, until this point (see FIG. 3A) the user can release the trigger 11 to open and reposition jaws 8,9. Just prior to locking, the protrusion 15 reaches the rib 7 and an increased tactile force is perceived by the user in actuating the trigger arm 18. The increased tactile force is a result of protrusions 3 on an arm 2 contacting rib 6 in housing 4. This indicates to the user that any additional force applied to the trigger arm 18 will require the user to complete the clip placement in order to release the jaws 8,9.

FIG. 4B corresponds to the stage just prior to locking. The jaws 8,9 are closed and the distal most clip has not been significantly advanced. Once the protrusion 15 engages with the rib 7 of the housing as shown in FIG. 3B, the trigger stroke must be completed.

FIG. 3B illustrates the end of the first stage and the initiation of the second stage of the trigger actuation. The protrusion has engaged with the rib 7 and the clip placement stage has been initiated (FIG. 3B).

Figure 5A:
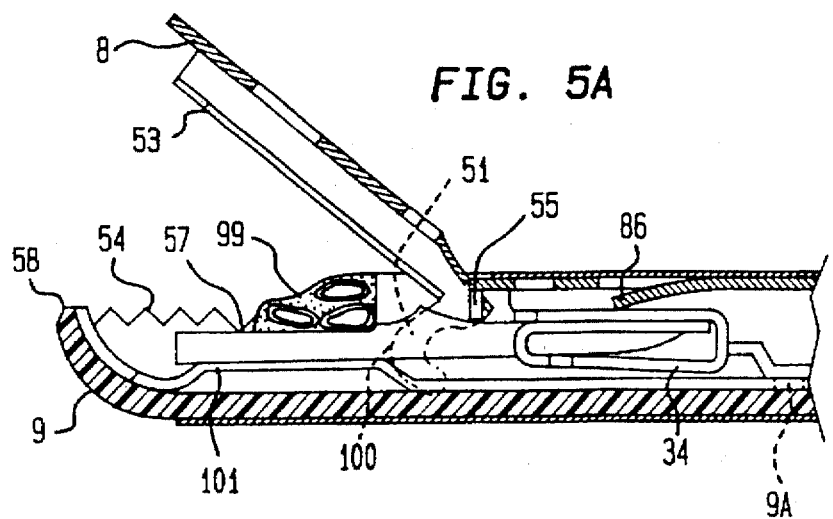
FIGS. 5A is a side cross sectional view of the distal end of the clip applier with jaws initially placed over a tissue structure to be ligated.
Figure 5B:
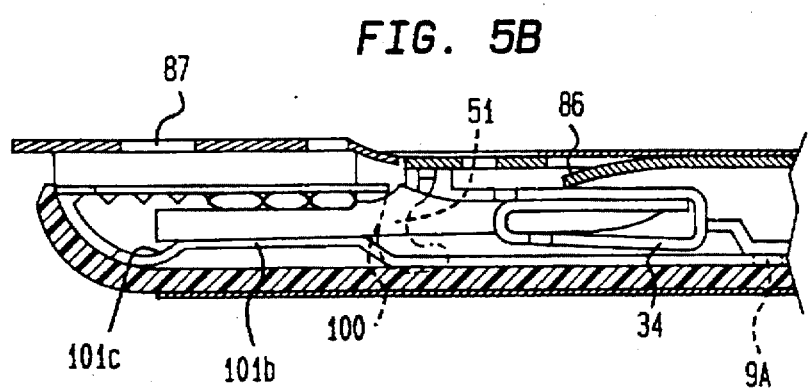
FIG. 5B is a side cross sectional view of the distal end of the clip applier with a tissue structure compressed between the jaws.
Figure 5C:
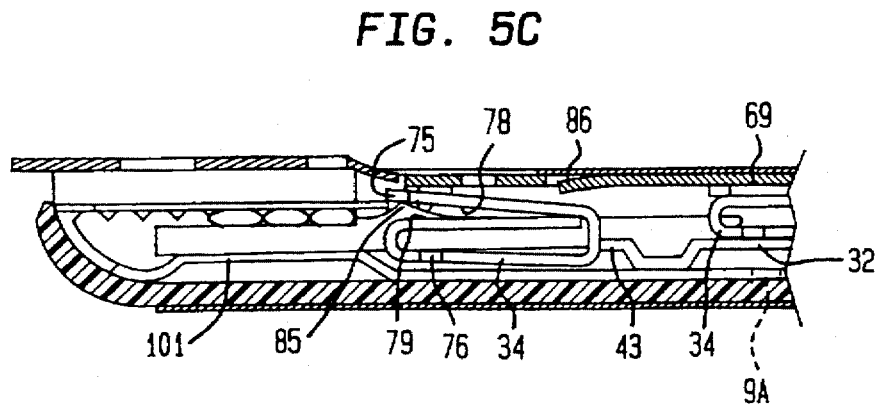
FIG. 5C is a side cross sectional view of the distal end of the clip applier with a clip advancing towards a compressed tissue structure.

FIG. 4B corresponds to the distal most clip advancing stage of the trigger actuation also illustrated in FIGS. 3B and 5C. The feed bar 32 is advanced distally before the slot 132 engages the downward tab 131 of the feed plate 130.

FIGS. 3C, 5D, 5E and 5F illustrate the continuation of the actuation with the clip stack 35 advancing as the slot 132 of the feed bar 32 engages the tab 131 of the feed plate 130 to advance the feed plate 130. The feed shoe 70 correspondingly advances the clip stack 35 the distance of one clip as the feed plate 130 advances. Transversely biased arms 74 move across walls 68 of grasper bar 31.

As shown in FIG. 5C, the distal clip 34 sits just proximally of tissue compressed by jaws 8,9 just after the first portion of the distal advancement occurs. The upper transverse tabs 75 of the first leg member 62 ride up ramps 91 to the top jaw 8, separating the inner tissue engaging surfaces 78, 79 of the biased leg members 62, 63 from each other to provide the opening 85.

Figure 3C:
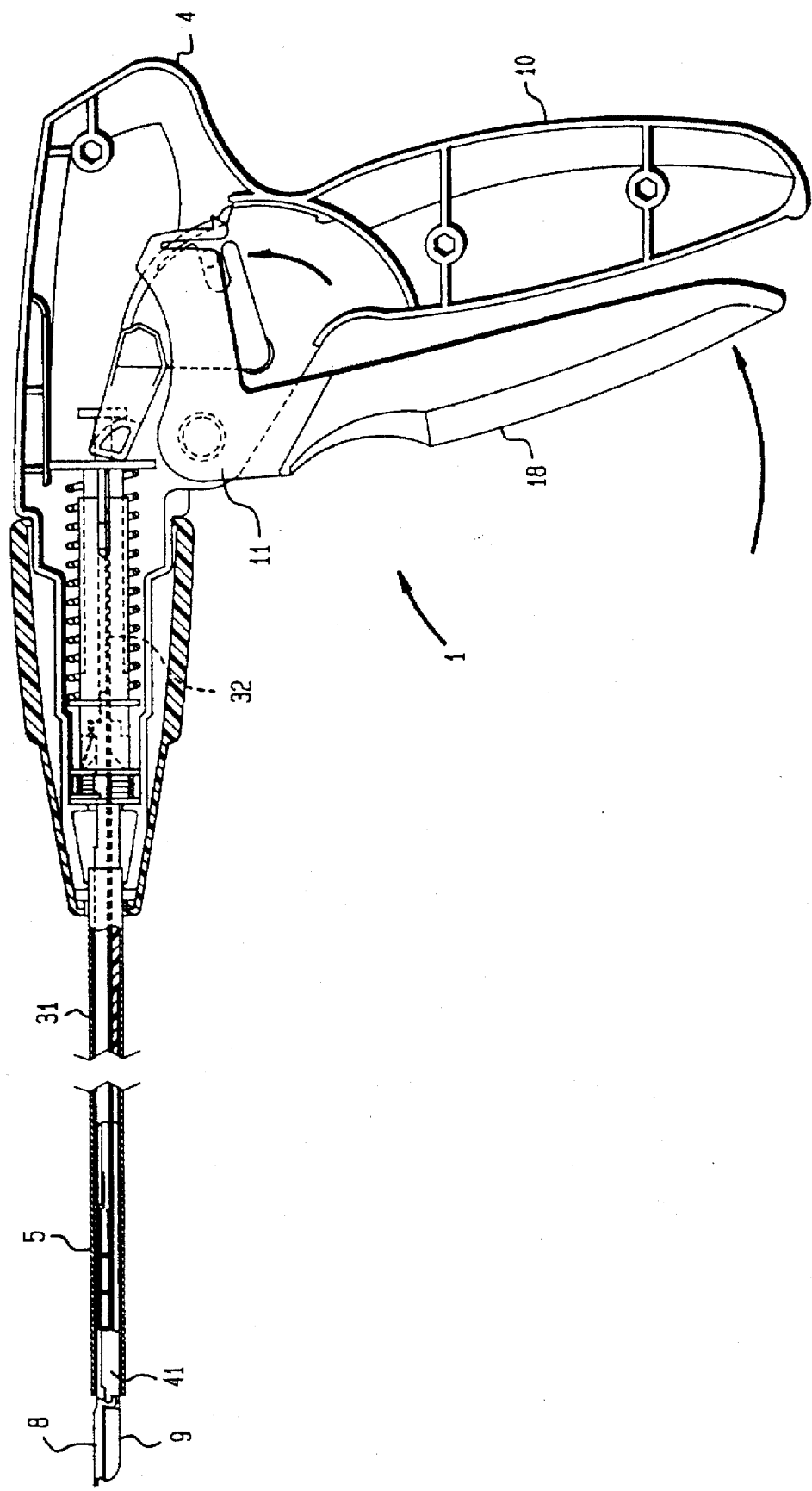
FIG. 3C is an enlarged cross sectional view of the clip applier of FIGS. 2A and 2B at the end of the clip advancement stage of trigger actuation.
Figure 5D:
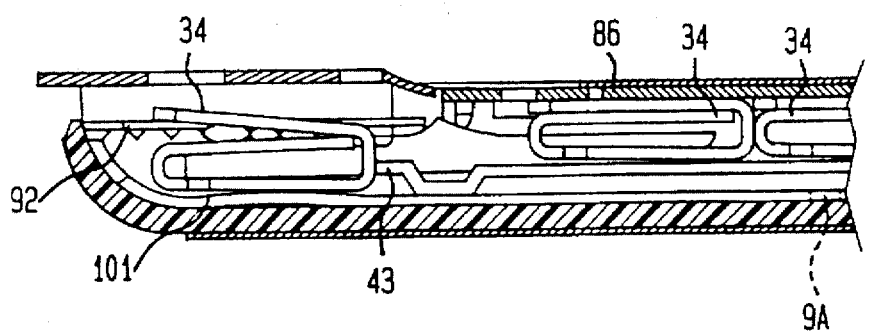
FIG. 5D is a side cross sectional view of the distal end of the clip applier with a clip placed over a tissue structure.
Figure 5E:
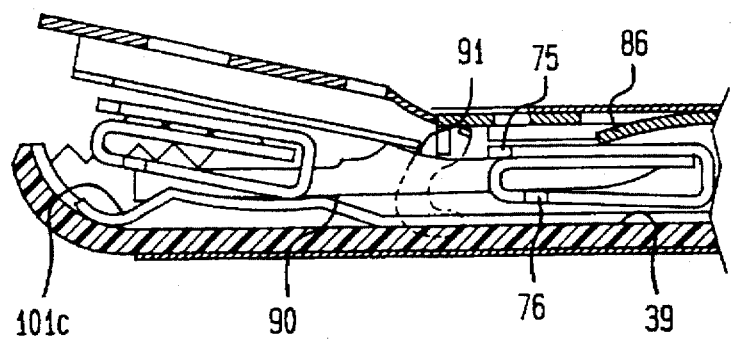
FIG. 5E is a side cross sectional view of the distal end of the clip applier with a clip placed over a tissue structure and a kick-off spring displacing the clip from the clip applier.
Figure 5F:
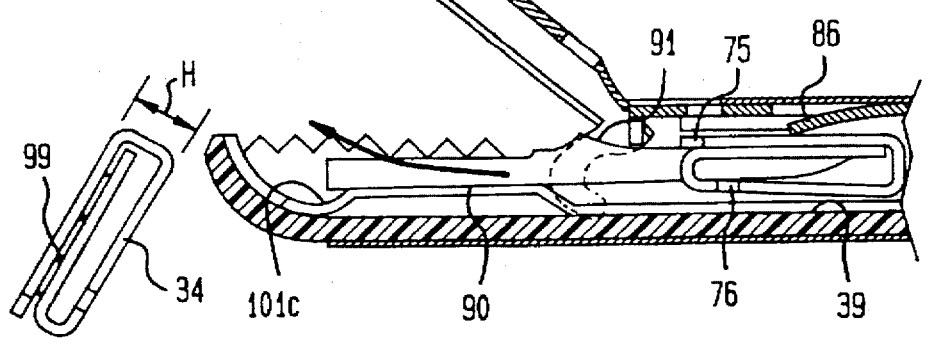
FIG. 5F is a side cross sectional view of the distal end of the clip applier with a clip placed over a tissue structure and the clip disengaged from the clip applier.

In FIG. 5D, the clip 34 is advanced over the tissue structure. In FIG. 5E, the clip begins to disengage from the jaws and the kickoff spring 101 pushes the clip out of the jaws while the distal surface 101c prevents the spring from sliding back into the jaw 9. In FIG. 5F, the clip is disengaged from the shelves 90, rails 92, jaws 8,9 at the distal end 40. This corresponds to the end of the trigger stroke, as illustrated in FIG. 3C. When the clip 34 is disengaged and the trigger arm 18 is released, the trigger 11 will return to its original position illustrated in FIG. 3A.

FIG. 4C illustrates the shaft of the instrument when the trigger is released after the end of the trigger stroke. The in line spring 23 causes the feed plate 130 and the feed bar 32 to retract. The biased arms 74 of the feed shoe 70, however, remain engaged against the notched surfaces 61 in the walls 38 of the lower jaw portion 41 so that the feed shoe 70 remains stationary. The lower arm 72 of the feed shoe 70 ramps out of the slot 60a in feed plate 130 in which it was positioned and into the slot 60b distal of slot 60a. Also, the next distal most clip is moved downward in front of the feed bar 32 as the feed bar 32 is retracted at the end of the trigger stroke. The cantilevered spring 86 prevents the clip from retracting into the feed bar 32. Thus, feed shoe 70, feed plate 130 and feed bar 32 are positioned to advance the next clip upon a subsequent actuation of the trigger 11.

The clips may be loaded and stored in the shaft as illustrated or, alternatively, in the handle, or, both shaft and handle. The applier may be capable of applying a plurality of clips as shown or a single clip. Also multiple clips may be simultaneously applied by adapting the device to accommodate multiple rows of clips and multiple disengagement means at the business end. A cutting means made be included in this embodiment, for cutting a ligated structure between two of the clips.

Referring now to FIGS. 13-16 there is illustrated an alternative embodiment of the present invention. An end effector 111 of a clip applying instrument is illustrated having: a shaft 105; a clip advancing fork 114 extending longitudinally through the lumen of a shaft 105; and a pair of pivotally attached hollow jaws 108, 109 coupled to the distal end of the shaft 105. The fork 114 has an upper prong 112 and a lower prong 113, respectively. Each prong 112,113 has a protrusion 116, 117 extending transversely from the prongs 112, 113. Each protrusion 116, 117 has a camming surface 118,119, respectively. The prongs 112,113 are respectively slidable within lumens 120,121 of jaws 108, 109. The lumens 120, 121 of the jaws 108, 109 include camming surfaces 128,129 corresponding to camming surfaces 118, 119 of protrusions 116, 117.

A partially formed deformable clip 122 is situated within the fork 114. The clip 122 has legs 123, 124 connected on their proximal end by a connecting member 125 and forming a narrow opening 126 on their distal end. The clip 122 is held by the legs 123,124 between the prongs 112, 113 of the fork 114.

The jaws 108, 109 are initially biased away from each other. As the clip fork 114 is advanced, the prongs 112, 113 are advanced through the lumens 120, 121. As the fork 114 is advanced, the clip leg 123 slides within the lumen 120 of the top jaw 108 and the clip leg 124 slides within the lumen 121 of the bottom jaw 109.

In use, a tissue structure to be ligated is placed between the jaws 108, 109. The clip fork 114 is advanced, closing the jaws 108,109 together and pre-compressing the tissue structure between the jaws 108,109. The fork 114 simultaneously advances the clip 122 over the precompressed tissue structure so that the tissue structure lies between the legs 123, 124 of the clip 122. The opening 126 of the semi-formed clip 122 is just sufficiently large enough to fit over a pre-compressed tissue structure and is small enough to fit within the shaft 105. Prior to any contact between camming surfaces 118, 119 and camming surfaces 128,129, the fork may be retracted, releasing the jaws 108, 109 from the tissue structure before the clip 122 is closed over the tissue structure.

As the clip fork 114 advances further, the camming surfaces 118,119 contact camming surfaces 128, 129 which force the prongs 112,113 to close together. As the prongs close, they in turn force the legs 123,124 of the clip 122 to close together over the pre-compressed tissue. The clip 122 is made of a deformable material. Thus when the clip 122 is closed, it is formed into its final shape and remains closed.

The clip fork 114 may be retracted, thereby opening the jaws 108,109, leaving the clip in place, ligating the tissue structure.

Ligating clips may be applied to blood vessels during a surgical procedure either as a single clip using a single clip applier or utilizing a multiple clip applier. The instrument may be inserted through a cannula during an endoscopic procedure and if a multiple clip applier is being used, the instrument may ligate or place clips on a number of vessels at a number of locations.

Figure 1:
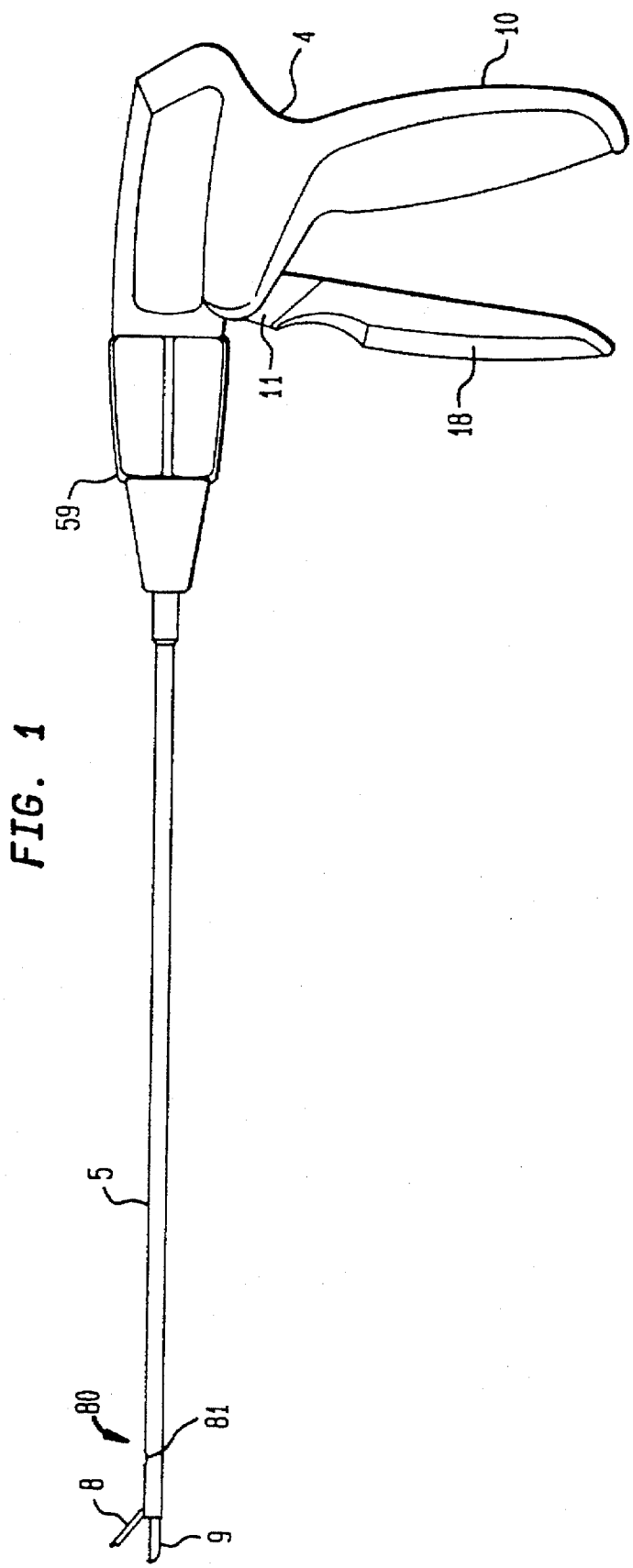
FIG. 1 is a side view of a clip applier of the present invention.
Figure 2A:
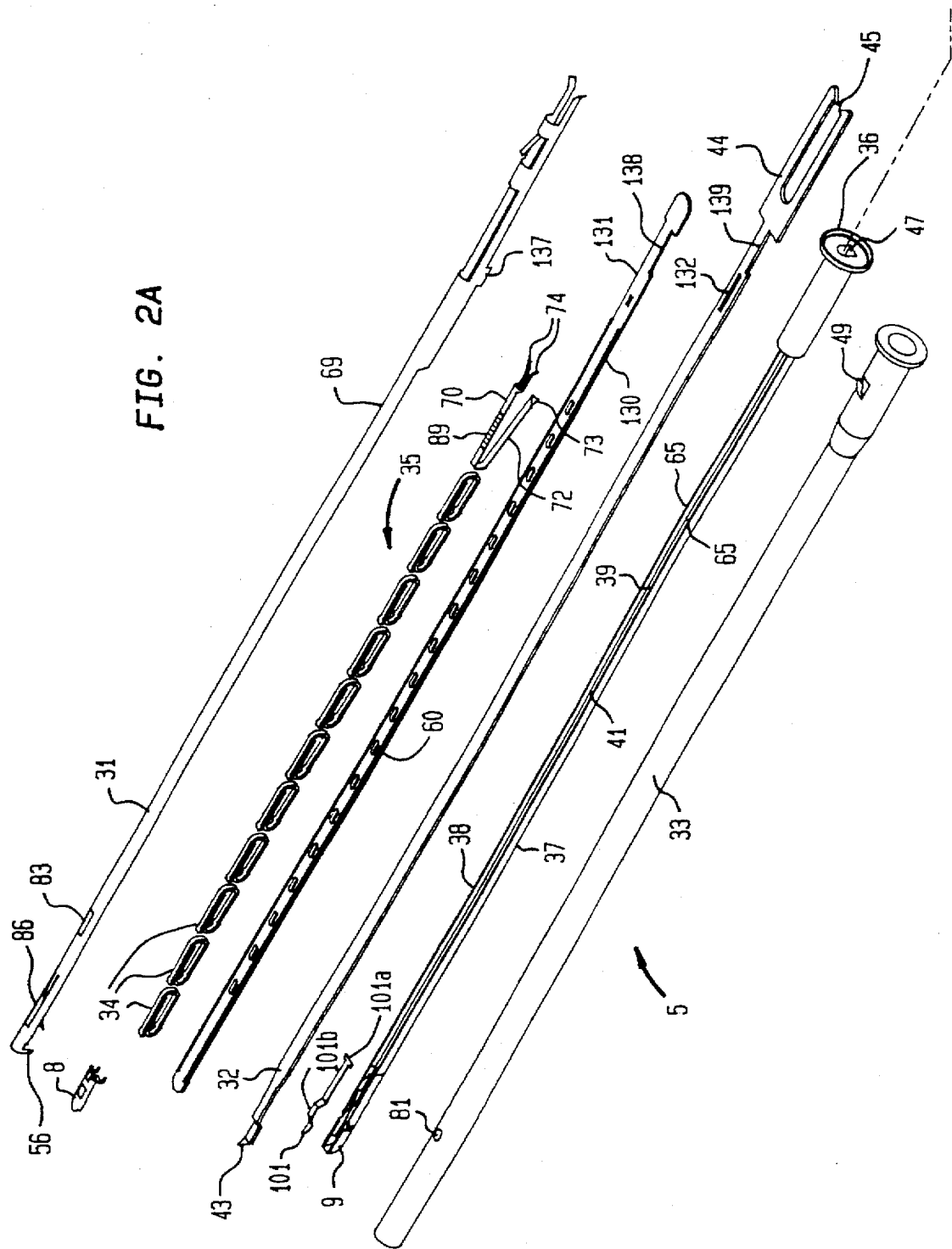
Figure 18:
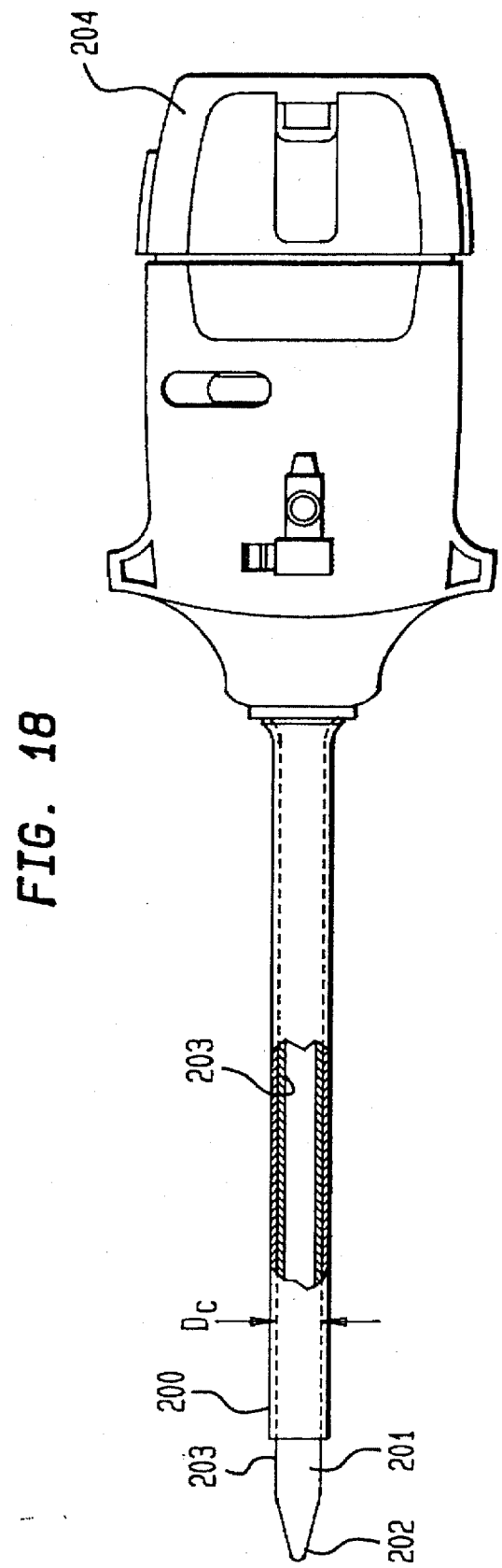
FIG. 18 illustrates a trocar and cannula of the present invention to be used in conjunction with an instrument of the present invention such as illustrated herein.

FIG. 18 illustrates a trocar 201 and cannula 200 of the present invention to be used as an access port through which the clip applier of FIG. 1 may be used. The cannula 200 has an inside diameter, $D_C$. The trocar 201 has a puncturing tip 202 coupled to a shaft 203 and a trocar handle 204. The trocar 201 is removably inserted through hollow tube of cannula 200 with puncturing tip 202 extending distally of the cannula tube 200. The trocar 201 and cannula 200 are used to puncture tissue to access a surgical site. The trocar 201 is removed to provide an access port through which the fastener instrument 10 may be inserted to treat tissue at the surgical site.

The cannula's inner diameter preferably has a size relationship to a closed clip height of a clip contained in the fastening instrument 10. Preferably the ratio of the cannula size (cannula inner diameter) to closed clip height is as close to unity as possible. For medium-large sized clips, the maximum ratio of cannula size to closed clip height is preferably about 2.7. The maximum ratio of cannula size to closed clip height for the medium sized clip is preferably about 3.2. The maximum ratio of cannula size to closed clip height for the small sized clip is preferably about 5.6. The clip sizes defined herein are intended to generally reflect the clip sizes known in the art and currently used in disposable clip appliers for laparoscopic and endoscopic surgery.

The instrument may be made from various materials such as metals, plastic preferably a polycarbonate resin and the like. Usually if the instrument is made from stainless steel the instrument will be reusable while if the instrument is made from plastic materials the instrument will be disposable. In certain embodiments of the instrument of the present invention, the instrument may be designed to accept a replaceable cartridge of clips. This may be accomplished with either a reusable instrument or semi-disposable instrument which is meant to be used a number of times on a single patient.

Having now described the present invention, it will be readily apparent to those skilled in the art that various modifications and alterations may be made to the present invention without departing from the spirit and scope thereof.

What is claimed is:

1. A tissue fastener applying instrument comprising:
   a housing:
   an actuator associated with said housing;
   a business end coupled to the housing and located at a distal end of the instrument, said business end comprising a tissue compressing portion movably coupled to said actuator to compress tissue at said business end; and a plurality of clips contained by said instrument, said clips each having an open position and a closed position and each clip being biased toward its closed position, said plurality of clips comprising a distal clip and a stack having a front end and a back end, said front end located adjacent said distal clip; and a clip feeder for advancing a clip towards the distal end of the clip feeder and for advancing a clip into said tissue compressing portion, for effecting movement of the clip to its open position around tissue compressed at said business end, with the clip thereafter moving to its closed position, said feeder comprising:

a distal clip feed element for advancing said distal clip into said business end for placement around tissue to be occluded;

a stack feed element having an initial position and an advanced position said stack feed element for advancing the stack towards the business end of the device as the stack feed element is moved from the initial position to the advanced position; and a ratchet element located at the back end of the stack, said ratchet element for advancing with movement of the stack feed element to the advanced position advancing the stack to an advanced stack position towards the business end of the device as the stack feed element is moved from the initial position to the advanced position, and for holding the stack in the advanced stack position when the stack feed element returns to the initial position.

2. The instrument of claim 1 wherein said stack feed element is movably coupled to said distal clip feed element.

3. The instrument of claim 2 wherein said distal clip feed element comprises a first distal stroke portion and a second distal stroke portion, wherein during said first distal stroke portion, said distal clip feed element advances distally independently of said stack feed element, and wherein during said second distal stroke portion, said distal clip feed element engageably advanced with the stack feed element.

4. In combination, a surgical access tube and an instrument for applying surgical fasteners comprising:

a hollow tube for accessing a surgical site within a patient, said tube having an inner diameter, and said instrument having a shaft positionable within said hollow tube; and a clip located in said instrument for applying surgical fasteners, said clip having a pair of leg members biased towards a closed position to define a closed fastener height corresponding to said closed position, said leg members defining therebetween a tissue occluding portion; said closed fastener height defined by the greatest height of said clip at said tissue occluding portion of said clip when said clip is closed;

said instrument including means for retaining one of said leg members against opening movement and means for effecting opening movement of the other one of said leg members while said one leg member is retained; and wherein said closed fastener height is such that the ratio of the tube inner diameter to the closed fastener height is less than or equal to 5.6.

5. The instrument and access tube of claim 4 wherein said closed fastener height is such that the ratio of the tube inner diameter to the closed fastener height is less than or equal to 3.2.

6. The instrument and access tube of claim 4 wherein said closed fastener height is such that the ratio of the tube inner diameter to the closed fastener height is less than or equal to 2.7.

7. The access tube and instrument of claim 4 wherein said access tube further comprises a trocar having a tissue dividing tip, said trocar removably inserted through said access tube inner diameter to expose said tip.

8. The access tube and instrument of claim 4 wherein said shaft comprises an actuating end and a fastener applying end opposite the actuating end;

said instrument further comprising a tissue compressing member located at the fastener applying end, for compressing tissue at the fastener applying end; and an actuator coupled to said tissue compressing member and extending through said shaft to said actuating end, said actuator for actuating said tissue compressing member.

9. An instrument for applying surgical clips comprising:

an instrument shaft having a lumen extending therethrough and a distal end;

opposed tissue compressing surfaces coupled to the distal end of the instrument shaft;

a clip advancer for advancing a clip to a first position around a tissue structure pressed between said surfaces; and a clip disengager compressed between said surfaces, said clip disengager comprising a spring arranged to lift said clip from said instrument, said disengager for releasing the fastener from the first position to a tissue ligating position around tissue compressed by said surfaces, wherein said spring includes a blocking portion arranged to prevent re-engagement of said fastener with said instrument.

10. An instrument for applying a plurality of surgical fasteners comprising:

a shaft having a distal end;

a fastener applying portion located at the distal end of the shaft, the fastener applying portion including tissue compressing surfaces;

a stack of fasteners located in said shaft, said stack having a distal end;

a distal-most fastener, adjacent said stack distal end;

a fastener feeder extending into said shaft said feeder engageable with said distal-most fastener to simultaneously advance the distal-most fastener around tissue compressed by said compressing surfaces and to distally advance said stack; and a disengager located at said fastener applying portion, said disengager comprising a spring arranged to lift said distal fastener from said fastener applying end, said spring including a blocking portion for preventing re-engagement of said distal fastener with said fastener applying end.

11. A surgical clip applying instrument comprising:

a housing;

an actuator associated with said housing;

a business end coupled to the housing and located at a distal end of the instrument; said business end comprising a pair of jaw members, each said jaw member having a tissue compressing surface to provide opposing tissue compressing surfaces, coupled to said actuator, said surfaces for precompressing tissue therebetween at least one of said jaw members comprising a tissue positioner comprised of interruptions in said surface of said at least one jaw member;

a surgical occlusion clip located in said instrument, said clip having a pair of leg members, at least one of which is movable relative to the other between an open position and a closed position, wherein said at least one leg member of said clip is biased in a closed direction;

a clip feeder disposed in said instrument, said clip feeder for advancing a clip in said closed position towards the distal end of the clip feeder, and into said business end, and for effecting relative movement of said at least one leg member of said clip to said open position around tissue compressed at said business end, wherein the actuator is operatively coupled to said feeder; and a clip disengaging portion on said business end of the instrument, for receiving, opening and then releasing said clip advanced by said clip feeder, in a position over tissue precompressed by said tissue compressing surfaces, wherein said clip disengaging portion releases said clip in a position over the precompressed tissue, said disengaging portion including a spring portion biasing a said leg member while the tissue is positioned between said leg members and as said clip is released from said business end.

* * * * *

UNITED STATES PATENT AND TRADEMARK OFFICE
CERTIFICATE OF CORRECTION

PATENT NO. : 5,681,330
DATED : October 28, 1997
INVENTOR(S) : J. David Hughett, David Stefanchik, Michael A. Murray, and C. Kerwin Braddock It is certified that error appears in the above-indentified patent and that said Letters Patent is hereby corrected as shown below:

Claim 3, Column 17, line 42 "advanced" should be -- advances --.

Signed and Sealed this

Third Day of March, 1998

Attest:

BRUCE LEHMAN

Attesting Officer

Commissioner of Patents and Trademarks